US008866610B2

(12) United States Patent
Riley et al.

(10) Patent No.: US 8,866,610 B2
(45) Date of Patent: Oct. 21, 2014

(54) HOSPITAL BED OBSTACLE DETECTION APPARATUS

(71) Applicant: Hill-Rom Services, Inc., Batesville, IN (US)

(72) Inventors: Carl W. Riley, Milan, IN (US); Keith A. Huster, Sunman, IN (US); Gregory J. Figel, Alpine, TX (US); Irvin J. Vanderpohl, III, Greensburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 13/957,575

(22) Filed: Aug. 2, 2013

(65) Prior Publication Data
US 2013/0312183 A1 Nov. 28, 2013

Related U.S. Application Data

(63) Continuation of application No. 13/600,872, filed on Aug. 31, 2012, now Pat. No. 8,502,663, which is a
(Continued)

(51) Int. Cl.
G08B 21/00 (2006.01)
A61G 7/05 (2006.01)
(Continued)

(52) U.S. Cl.
CPC ............ *A61G 7/05* (2013.01); *A47C 19/045* (2013.01); *A61B 5/1115* (2013.01); *A61G 7/00* (2013.01); *A61G 7/005* (2013.01); *A61G 7/008* (2013.01); *A61G 7/012* (2013.01); *A61G 7/015* (2013.01); *A61G 7/018* (2013.01); *A61G 7/0507* (2013.01); *A61G 7/05715* (2013.01); *A61G 7/05759* (2013.01); *B60B 33/0005* (2013.01); *B60B 33/0039* (2013.01); *B60B 33/0049* (2013.01); *B60B 33/0057* (2013.01); *B60B 33/0068* (2013.01); *B60B 33/0073* (2013.01); *B60B 33/021* (2013.01); *H01H 3/16* (2013.01); *A61G 2007/0513* (2013.01); *A61G 2007/0527* (2013.01); *A61G 2203/72* (2013.01); *A61G 2203/74* (2013.01); *A61G 2203/34* (2013.01); *A61G 2203/726* (2013.01); *H01H 3/412* (2013.01)
USPC ............ 340/540; 5/600; 5/618; 5/611; 5/424; 5/624; 340/686.1; 340/507

(58) Field of Classification Search
USPC ........................................ 340/540; 5/600, 618
See application file for complete search history.

(56) References Cited

U.S. PATENT DOCUMENTS 1,078,077 A 11/1913 Arnold
2,527,111 A 10/1950 Widrich et al.
(Continued)

FOREIGN PATENT DOCUMENTS

DE 3313843 A1 10/1984
DE 3716917 A1 12/1988
(Continued)

OTHER PUBLICATIONS

European Search Report for EP 09 00 2423 dated Aug. 4, 2009.
(Continued)

Primary Examiner — Jack K Wang
(74) Attorney, Agent, or Firm — Barnes & Thornburg LLP

(57) ABSTRACT

A hospital bed obstacle detection device and related method for detecting an obstacle between first and second components of a hospital bed is provided.

19 Claims, 25 Drawing Sheets

Related U.S. Application Data continuation of application No. 12/347,124, filed on Dec. 31, 2008, now Pat. No. 8,258,944, which is a continuation of application No. 10/510,996, filed as application No. PCT/US03/12166 on Apr. 21, 2003, now Pat. No. 7,472,437.

(60) Provisional application No. 60/373,819, filed on Apr. 19, 2002, provisional application No. 60/408,698, filed on Sep. 6, 2002.

(51) Int. Cl.
| | |
|---|---|
| *A47C 19/04* | (2006.01) |
| *A61B 5/11* | (2006.01) |
| *A61G 7/00* | (2006.01) |
| *A61G 7/005* | (2006.01) |
| *A61G 7/008* | (2006.01) |
| *A61G 7/012* | (2006.01) |
| *A61G 7/015* | (2006.01) |
| *A61G 7/018* | (2006.01) |
| *A61G 7/057* | (2006.01) |
| *B60B 33/00* | (2006.01) |
| *B60B 33/02* | (2006.01) |
| *H01H 3/16* | (2006.01) |
| *A47B 71/00* | (2006.01) |
| *A47B 7/02* | (2006.01) |
| *A47B 7/00* | (2006.01) |
| *A47C 27/08* | (2006.01) |
| *G08B 29/00* | (2006.01) |

(56) References Cited

U.S. PATENT DOCUMENTS

| | | | |
|---|---|---|---|
| 2,900,521 A | 8/1959 | Eames | |
| 3,704,396 A | 11/1972 | Macdonald | |
| 3,742,222 A | 6/1973 | Endl | |
| 3,746,863 A | 7/1973 | Pronovost | |
| 3,805,061 A | 4/1974 | De Missimy et al. | |
| 3,858,043 A | 12/1974 | Sick et al. | |
| 3,875,403 A | 4/1975 | Svensson | |
| 3,970,846 A | 7/1976 | Schofield, Jr. et al. | |
| 4,266,124 A | 5/1981 | Weber et al. | |
| 4,325,061 A | 4/1982 | Wolar | |
| 4,385,508 A | 5/1983 | Schimko | |
| 4,403,214 A | 9/1983 | Wolar | |
| 4,463,463 A | 8/1984 | Kaneko | |
| 4,520,262 A | 5/1985 | Denton | |
| 4,534,077 A | 8/1985 | Martin | |
| 4,552,403 A | 11/1985 | Yindra | |
| 4,645,920 A | 2/1987 | Carroll et al. | |
| 4,724,554 A | 2/1988 | Kowalski et al. | |
| 4,794,248 A | 12/1988 | Gray | |
| 4,837,877 A | 6/1989 | Hamada et al. | |
| 4,882,566 A | 11/1989 | Koerber, Sr. et al. | |
| 4,921,295 A | 5/1990 | Stollenwerk | |
| 4,960,271 A | 10/1990 | Sebring | |
| 5,020,169 A | 6/1991 | Hamada et al. | |
| RE33,668 E | 8/1991 | Gray | |
| 5,156,166 A | 10/1992 | Sebring | |
| 5,181,288 A | 1/1993 | Heaton et al. | |
| 5,280,622 A * | 1/1994 | Tino | 700/255 |
| 5,317,769 A | 6/1994 | Weismiller et al. | |
| 5,468,216 A | 11/1995 | Johnson et al. | |
| 5,495,228 A | 2/1996 | Futsuhara et al. | |
| 5,567,931 A | 10/1996 | Amend et al. | |
| 5,696,362 A | 12/1997 | Amend | |
| 5,758,371 A | 6/1998 | VanDyke et al. | |
| 5,984,404 A | 11/1999 | Novoa et al. | |
| 6,167,991 B1 * | 1/2001 | Full et al. | 187/317 |
| 6,199,508 B1 | 3/2001 | Miale et al. | |
| 6,208,250 B1 * | 3/2001 | Dixon et al. | 340/573.1 |
| 6,320,510 B2 | 11/2001 | Menkedick et al. | |
| 6,351,861 B1 | 3/2002 | Shows et al. | |
| 6,354,716 B1 | 3/2002 | Chen et al. | |
| 6,662,391 B2 | 12/2003 | Wilson et al. | |
| 6,791,460 B2 | 9/2004 | Dixon et al. | |
| 6,983,499 B2 | 1/2006 | Gladney | |
| 7,089,612 B2 | 8/2006 | Rocher et al. | |
| 7,296,312 B2 | 11/2007 | Menkedick et al. | |
| 7,472,437 B2 | 1/2009 | Riley et al. | |
| 8,258,944 B2 | 9/2012 | Riley et al. | |
| 8,502,663 B2 | 8/2013 | Riley et al. | |
| 2001/0032362 A1 | 10/2001 | Welling et al. | |
| 2002/0002742 A1 | 1/2002 | Osborne et al. | |
| 2002/0080037 A1 | 6/2002 | Dixon et al. | |
| 2004/0177445 A1 | 9/2004 | Osborne et al. | |
| 2004/0231052 A1 | 11/2004 | Gladney | |
| 2005/0035871 A1 | 2/2005 | Dixon et al. | |
| 2005/0166324 A1 | 8/2005 | Dixon et al. | |
| 2005/0172405 A1 | 8/2005 | Menkedick et al. | |
| 2006/0010601 A1 | 1/2006 | Riley et al. | |
| 2006/0080777 A1 | 4/2006 | Rocher et al. | |
| 2006/0107459 A1 | 5/2006 | Gladney | |
| 2006/0162079 A1 | 7/2006 | Menkedick et al. | |
| 2006/0168730 A1 | 8/2006 | Menkedick et al. | |
| 2006/0168731 A1 | 8/2006 | Menkedick et al. | |
| 2007/0296600 A1 | 12/2007 | Dixon et al. | |
| 2008/0010748 A1 | 1/2008 | Menkedick et al. | |
| 2012/0317726 A1 | 12/2012 | Riley et al. | |

FOREIGN PATENT DOCUMENTS

| | | |
|---|---|---|
| FR | 2770396 A1 | 5/1999 |
| GB | 2 343 371 A | 5/2000 |
| JP | 2-156950 | 6/1990 |
| JP | 11299837 | 11/1999 |
| WO | 9627356 A1 | 9/1996 |
| WO | WO9720534 | 6/1997 |
| WO | 0147340 A2 | 7/2001 |

OTHER PUBLICATIONS

Prior Art emme3 Bed Brochure, purported by Defendants to have been published circa Mar. 1996 ("emme3 Bed Brochure Italian").

Prior Art emme3 Bed Brochure, purported by Defendants to have been published circa May 1997 ("emme3 Bed Brochure English").

Prior Art emme3 Instructions for Use, purported by Defendants to have been published circa Mar. 1998 ("emme3 Instructions").

Complaint (filed Jun. 17, 2010 by Plaintiffs, Hill-Rom, Inc. Hill-Rom Services and Hill-Rom Company).

Answer and Counterclaims of Defendants Huntleigh Healthcare LLC and Huntleigh Healthcare, Inc. To the Complaint of Hill-Rom, Inc., Hill-Rom Services, Inc. and Hill-Rom Company, Inc. (filed Aug. 5, 2010 by Defendants Huntleigh Healthcare LLC and Huntleigh Healthcare, Inc.).

Reply to Counterclaims (filed Aug. 16, 2010 by Plaintiffs, Hill-Rom, Inc. Hill-Rom Services and Hill-Rom Company).

Plaintiff Hill-Rom's First Set of Interrogatories to Defendant (filed Sep. 17, 2010 by Plaintiffs, Hill-Rom, Inc. Hill-Rom Services and Hill-Rom Company).

Plaintiff Hill-Rom's First Request for Production of Documents and Things to Defendant Huntleigh (filed Sep. 17, 2010 by Plaintiffs, Hill-Rom, Inc. Hill-Romm Services and Hill-Rom Company).

Huntleigh Healthcare LLC's First Request to Hill-Rom Services, Inc. for Production of Documents and Things (filed Sep. 22, 2010 by Defendants Hunleigh Healthcare LLC and Huntleigh Healthcare, Inc.).

Huntleigh Healthcare LLC's First Request to Hill-Rom Company, Inc. for Production of Documents and Things (filed Sep. 22, 2010 by Defendants Huntleigh Healthcare LLC and Huntleigh Healthcare, Inc.).

Huntleigh Healthcare LLC's First Request to Hill-Rom, Inc. for Production of Documents and Things (filed Sep. 22, 2010 by Defendants Huntleigh Healthcare LLC and Huntleigh Healthcare, Inc.).

Defendant Huntleigh Healthcare LLC's First Set of Interrogatories (Nos. 1-11) to Plaintiff Hill-Rom Company, Inc. (filed Sep. 22, 2010 by Defendants Huntliegh Healthcare, LLC and Huntleigh Healthcare, Inc.).

(56) References Cited

OTHER PUBLICATIONS

Defendant Huntleigh Healthcare LLC's First Set of Interrogatories (Nos. 1-11) to Plaintiff Hill-Rom Services, Inc. (filed Sep. 22, 2010 by Defendants Hunleigh Healthcare LLC and Huntleigh Healthcare, Inc.).
Defendant Huntleigh Healthcare LLC's First Set of Interrogatories (Nos. 1-11) to Plaintiff Hill-Rom, Inc. (filed Sep. 22, 2010 by Defendants Hunleigh Healthcare LLC and Huntleigh Healthcare, Inc.).
Hill-Rom's Initial Disclosres (filed Sep. 30, 2010 by Plaintiffs, Hill-Rom, Inc. Hill-Rom Services and Hill-Rom Company).
Initial Disclosures for Defendants Huntleigh Healthcare, LLC and Huntleigh Healthcare, Inc. (filed Sep. 30, 2010 by Defendants Huntleigh Healthcare, LLC and Huntleigh Healthcare, Inc.
Case Management Plan Order (filed Nov. 5, 2010).
Plaintiffs Preliminary Infringement Contentions (filed Nov. 5, 2010 by Plaintiffs, Hill-Rom, Inc. Hill-Rom Services and Hill-Rom Company).
Responses and Objections of Defendants Huntleigh Healthcare, LLC and Huntleigh Healthcare, Inc. to Plaintiff Hill-Rom's First Set of Interrogatories (1-5) (filed Nov. 18, 2010 by Defendants Huntleigh Healthcare, LLC and Huntleigh Healthcare, Inc.).
Responses and Objections of Defendants Huntleigh Healthcare, LLC and Huntleigh Healthcare, Inc. to Plaintiff Hill-Rom's First Request for Documents and Things (filed Nov. 18, 2010 by Defendants Huntleigh Healthcare, LLC and Huntleigh Healthcare, Inc.).
Plaintiffs Hill-Rom, Inc's Hill-Rom Services, Inc's and Hill-Rom Company, Inc's Consolidated Answeres and Objections to Defendant Huntleigh Healthcare, LLC's First Set of Interrogatories (Nos. 1-11) (filed Nov. 22, 2010 by Plaintiffs Hill-Rom, Inc. Hill-Rom Services and Hill-Rom Company).
Plaintiffs Hill-Rom, Inc's Hill-Rom Services, Inc's and Hill-Rom Company, Inc's Consolidated Responses and Objections to Defendant Huntleigh Healthcare, LLC's First Request for Production of Documents and Things (filed Nov. 22, 2010 by Plaintiffs Hill-Rom, Inc. Hill-Rom Services and Hill-Rom Company).
Defendants Preliminary Invalidity Contentions (filed Dec. 22, 2010 by Defendants Huntleigh Healthcare, LLC and Huntleigh Healthcare, Inc.)—Exhibits A-H.
European search report from EP 10 01 1366 dated Mar. 14, 2014, 7 pages.

* cited by examiner

HOSPITAL BED OBSTACLE DETECTION APPARATUS

This application is a continuation of U.S. application Ser. No. 13/600,872, filed Aug. 31, 2012, now projected U.S. Pat. No. 8,502,663, which is a continuation of U.S. application Ser. No. 12/347,124, filed Dec. 31, 2008, now U.S. Pat. No. 8,258,944, which is a continuation of U.S. application Ser. No. 10/510,996, filed Jul. 20, 2005, now U.S. Pat. No. 7,472,437, issue date Jan. 6, 2009, and which is the national phase under 35 U.S.C. §371 of PCT International Application No. PCT/US03/12166, which has an International filing date of Apr. 21, 2003, designating the United States of America, and claims the benefit of U.S. Provisional Patent Application No. 60/373,819, which was filed Apr. 19, 2002, and U.S. Provisional Patent Application No. 60/408,698, which was filed Sep. 6, 2002.

BACKGROUND

It is well known to provide a vertically movable patient support. More particularly, it is known to provide a hospital bed including a base frame and an elevating frame supporting a patient support surface. A lifting mechanism is configured to raise and lower the elevating frame relative to the base frame. Entry and exit from the bed is facilitated by placing the elevating frame in a lowered position. A raised position of the elevating frame, in turn, provides a convenient surface for the examination and treatment of the patient.

Additionally, conventional lifting mechanisms provide for the tilting of the elevating frame from a horizontal position into Trendelenburg and reverse Trendelenburg positions. A hospital bed incorporating such a lifting mechanism is illustrated in U.S. Pat. No. 3,958,283 to Adams et al., the disclosure of which is expressly incorporated by reference herein.

SUMMARY

The present invention relates generally to a patient support and, more particularly, to a device and related method for detecting obstacles within a path of travel intermediate first and second components of a hospital bed. Further, the present invention relates to a device and related method for inhibiting the relative movement between first and second components of the hospital bed upon detection of an obstacle within the path of travel.

According to an illustrative embodiment of the invention, a hospital bed obstacle detection device is provided for use with a hospital bed including a base frame and an elevating frame coupled to a patient support surface. The obstacle detection device controls movement of the elevating frame relative to the base frame upon detecting an object within a path of travel of the elevating frame. The obstacle detection device comprises an emitter coupled to one of the base frame and the elevating frame. The emitter is configured to generate a wireless curtain extending below the elevating frame. The obstacle detection device further comprises a receiver coupled to one of the base frame and the elevating frame of the bed. The receiver is configured to detect the wireless curtain generated by the emitter. The obstacle detection device further comprises a control unit in communication with the receiver and configured to control movement of the elevating frame based on an output signal from the receiver.

Illustratively according to the invention, the emitter comprises an infrared light source and a lens positioned proximate the infrared light source configured to convert light emitted therefrom to form an optical curtain. Illustratively, the lens comprises a fresnel lens.

Further illustratively according to the invention, the wireless curtain includes a modulated signal and the receiver compares the modulated signal to a predefined verification signal in order to prevent interference from external light sources.

Illustratively according to the invention, the receiver is configured to move with the elevating frame within a predefined vertical range. The predefined vertical range is illustratively from the base frame to the elevating frame when the elevating frame is in a fully raised position.

Further illustratively according to the invention, an indicator is provided in communication with the control unit. The indicator is configured to indicate failure of the receiver to detect the wireless curtain.

According to a further illustrative embodiment of the invention, a patient support apparatus comprises a base frame, an elevating frame configured to move along a path of travel above the base frame, a patient support surface supported by the elevating frame, and a detector supported by one of the elevating frame and the base frame, the detector being configured to detect an obstacle within the path of travel of the elevating frame and provide a control signal in response thereto. A control unit is provided in communication with the detector and is configured to prevent movement of the elevating frame in response to the control signal.

Illustratively according to the invention, an emitter is supported by one of the base frame and the elevating frame, wherein the emitter is configured to generate a wireless signal.

Further illustratively according to the invention, the emitter is supported by the base frame and the detector is supported for movement with the elevating frame.

Illustratively according to the invention, the detector comprises a camera configured to capture images of the elevating frame along the path of travel. The control unit is configured to compare the images captured by the camera to predefined images to determine the presence of an obstacle within the path of travel.

According to another illustrative embodiment of the invention, a patient support apparatus comprises a base frame, an elevating frame disposed in spaced relation to the base frame, a patient support surface supported by the elevating frame, and an emitter coupled to one of the base frame and the elevating frame and configured to generate a wireless signal. A receiver is coupled to one of the base frame and the elevating frame and is configured to detect the wireless signal.

Illustratively according to the invention, the patient support apparatus includes a lifting device configured to move the elevating frame relative to the base frame.

Further illustratively according to the invention, the patient support apparatus includes a control unit in communication with the lifting device and the receiver. The control unit is configured to prevent operation of the lifting device if the receiver fails to detect the wireless signal.

Illustratively according to the invention, the emitter generates an optical curtain positioned intermediate the base frame and the elevating frame. The emitter illustratively comprises an infrared light source and a lens is positioned proximate the infrared light source configured to convert light emitted therefrom to the optical curtain. Illustratively, the lens comprises a fresnel lens.

Further illustratively according to the invention, the wireless signal includes a modulated signal and the control unit compares the modulated signal to a predefined verification signal in order to prevent interference from external light sources.

Further illustratively according to the invention, the receiver is configured to move with the elevating frame within a predefined vertical range. The predefined vertical range is illustratively from the base frame to the elevating frame when the elevating frame is in a fully raised position.

Illustratively according to the invention, an indicator is provided in communication with the control unit. The indicator is configured to indicate failure of the receiver to detect a wireless signal.

Further illustratively according to the invention, the wireless signal includes a pulsed portion having a predefined frequency, and said receiver is configured to detect said predefined frequency. The pulsed portion illustratively has a frequency of approximately 57 MHz and has a duration of approximately 600 microseconds followed by a delay of approximately 2 milliseconds.

Further illustratively according to the invention, the emitter is configured to generate a plurality of wireless signals in a plurality of signal paths, and a plurality of receivers are configured to detect the wireless signals along different ones of the signal paths. The control unit is configured to prevent movement of the elevating frame when any of the plurality of receivers fail to detect a wireless signal.

Illustratively according to the invention, at least one of the receivers is supported for movement with the elevating frame and the emitter is supported by the base frame.

According to another illustrative embodiment of the invention, a hospital bed obstacle detection device is provided for use with a hospital bed including a base frame and an elevating frame coupled to a patient support surface. The obstacle detection device is configured to prevent vertical movement of the elevating frame relative to the base frame upon detecting an object within a path of travel of the elevating frame. The obstacle detection device comprises at least one emitter configured to generate a first optical curtain extending proximate a first longitudinal side edge of the bed intermediate the base frame and the elevating frame, and a second optical curtain extending proximate a second longitudinal side edge of the bed intermediate the base frame and the elevating frame. The obstacle detection device further comprises at least one first side receiver associated with the at least one emitter and configured to detect the first optical curtain, and at least one second side receiver associated with the at least one emitter and configured to detect the second optical curtain. A control unit is provided in communication with the at least one first side receiver and the at least one second side receiver, the control unit configured to prevent movement of the elevating frame if either of the at least one first side receiver and the at least one second side receiver does not detect the first optical curtain and the second optical curtain, respectively.

Illustratively according to the invention, the emitter comprises an infrared light source and a lens positioned proximate the infrared light source configured to convert light emitted therefrom to the optical curtain. Illustratively, the lens comprises a fresnel lens.

Illustratively according to the invention, each optical curtain includes a modulated signal and each receiver compares the modulated signal to a predefined verification signal to prevent interference from external light sources.

Further illustratively according to the invention, each receiver is configured to move with the elevating frame within a predefined vertical range. The predefined vertical range is illustratively from the base frame to the elevating frame when the elevating frame is in a fully raised position.

Illustratively according to the invention, an indicator is provided in communication with the control unit. The indicator is configured to indicate failure of either of the first side and the second side receivers to detect the first and second optical curtains, respectively.

According to a further illustrative embodiment of the present invention, a hospital bed obstacle detection device is provided for use with a hospital bed including a base frame and an elevating frame coupled to a patient support surface. The obstacle detection device controls movement of the elevating frame relative to the base frame upon detecting an object within a path of travel of the elevating frame. The obstacle detection device comprises means for generating a wireless curtain within a path of travel of the elevating frame, means for detecting the wireless curtain and generating a signal in response thereto, and means for receiving the signal and controlling movement of the elevating frame in response thereto.

Illustratively according to the invention, the means for generating a wireless curtain comprises an infrared light source. A lens is illustratively positioned proximate the infrared light source and is configured to convert light emitted therefrom to the wireless curtain. Illustratively the lens comprises a fresnel lens.

Further illustratively according to the invention, the wireless curtain includes a modulated signal and the detecting means compares the modulated signal to a predefined signal to prevent interference from external light sources.

Further illustratively according to the invention, the detecting means is configured to move with the elevating frame within a predefined vertical range. The predefined vertical range is illustratively from the base frame to the elevating frame when the elevating frame is in a fully raised position.

Illustratively according to the invention, an indicating means is provided in communication with the control means. The indicating means is configured to indicate failure of the detecting means to detect the wireless curtain.

According to another illustrative embodiment of the invention, a method is provided of preventing vertical movement of a patient support surface upon detection of an obstacle within a path of travel, the method comprising the steps of providing a patient support including a movable component, generating a detectable wireless signal within a path of travel of the movable component, providing a receiver for detecting the wireless signal, moving the patient support surface, generating a stop signal if the receiver fails to detect the wireless signal, and preventing vertical movement of the patient support surface in response to the stop signal.

Illustratively according to the invention, the step of generating a detectable wireless signal comprises the steps of providing a light source and emitting infrared light from the light source. The method illustratively further comprises the step of placing a lens proximate the light source for converting light emitted therefrom to an optical curtain.

Further illustratively according to the invention, the wireless signal includes a modulated signal and the receiver compares the modulated signal to a predefined verification signal to prevent interference from external light sources.

Illustratively according to the invention, the receiver is configured to move with the elevating frame within a predefined vertical range.

Further illustratively according to the invention, the method comprises the step of activating an indicator in response to the stop signal.

According to a further illustrative embodiment of the invention, a hospital bed includes a first component, a second component movable relative to the first component, an optical curtain generator coupled to the first component, and an optical curtain detector coupled to the second component. The hospital bed further includes a control unit in communication with the detector and being configured to prevent relative movement of the first and second portions upon failure of the detector to detect the optical curtain.

Illustratively according to the invention, the first component is one of an elevating frame and an articulating deck supported by the elevating frame, and the second component is the other of the elevating frame and the articulating deck.

Illustratively according to the invention, the first component is one of a base frame and an elevating frame supported by the base frame, and the second component is the other of the base frame and the elevating frame.

Illustratively according to the invention, the first component is a first siderail and the second component is a second siderail.

Illustratively according to the invention, the first component is one of an elevating frame and a siderail supported by the elevating frame, and the second component is the other of the elevating frame and the siderail.

Illustratively according to the invention, the first component is one of a footboard and a siderail, and the second component is the other of the footboard and the siderail.

According to another illustrative embodiment of the invention, a hospital bed includes a first component, a second component configured to move relative to the first portion along a path of travel, and a detector supported by one of the first component and the second component, the detector configured to detect an obstacle within the path of travel of the second component and provide a control signal in response thereto. A control unit is in communication with the detector and is configured to prevent relative movement of the first and second components in response to the control signal.

Illustratively according to the invention, an emitter is supported by one of the first component and the second component, the emitter being configured to generate a wireless signal. The emitter is illustratively supported by the first component and the detector is supported for movement with the second component.

Further illustratively according to the invention, the detector comprises a camera configured to capture images of the second component along the path of travel. The control unit is configured to compare the images captured by the camera to predefined images to determine the presence of an obstacle within the path of travel.

According to a further illustrative embodiment of the invention, a patient support apparatus comprises a first component, a second component configured to move relative to the first component along a path of travel, and an emitter supported by one of the first component and the second component. The emitter is configured to transmit a wireless signal having a pulsed portion of a predetermined frequency and duration. A detector is configured to detect the wireless signal, the detector being configured to provide an indication if it fails to detect the pulsed portion of the wireless signal.

Illustratively according to the invention, a control unit is configured to prevent movement of the second component relative to the first component when the detector fails to detect the pulsed portion of the wireless signal. Further illustratively, the pulsed portion of the wireless signal has a frequency of approximately 57 MHz and a duration of approximately 600 microseconds.

According to another illustrative embodiment of the invention, a patient support apparatus comprises a first component, a second component configured to move relative to the first component along a path of travel, and a force sensing switch supported by one of the first component and the second component. The force sensing switch is configured to provide an indication if it detects the application of a predetermined force thereto.

Illustratively according to the invention, a control unit is configured to prevent movement of the second component relative to the first component when the force sensing switch detects the application of the predetermined force.

Additional features and advantages of the present invention will become apparent to those skilled in the art upon a consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
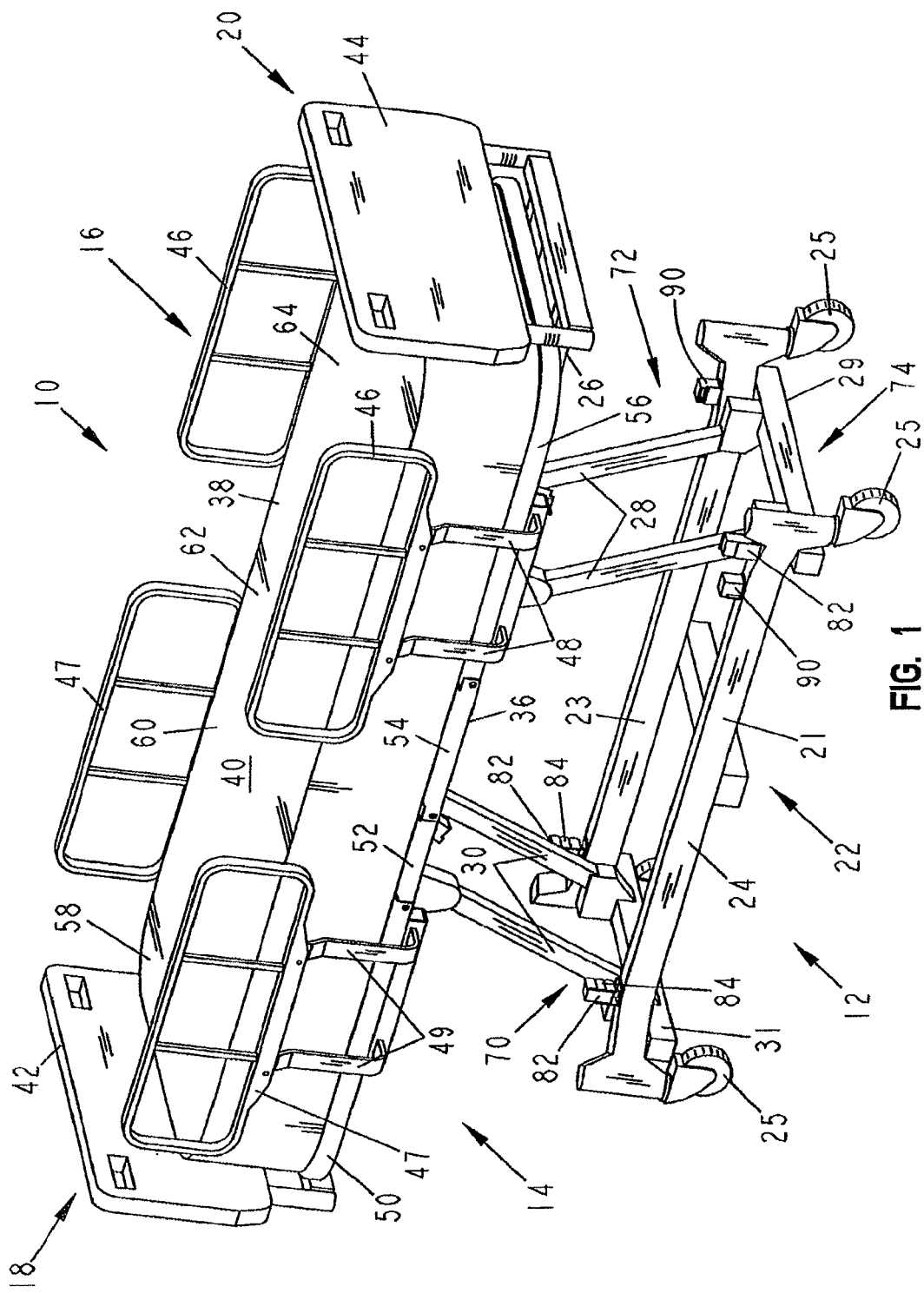
FIG. 1 is a perspective view of a hospital bed incorporating an illustrative embodiment of the obstacle detection device of the present invention.
Figure 2:
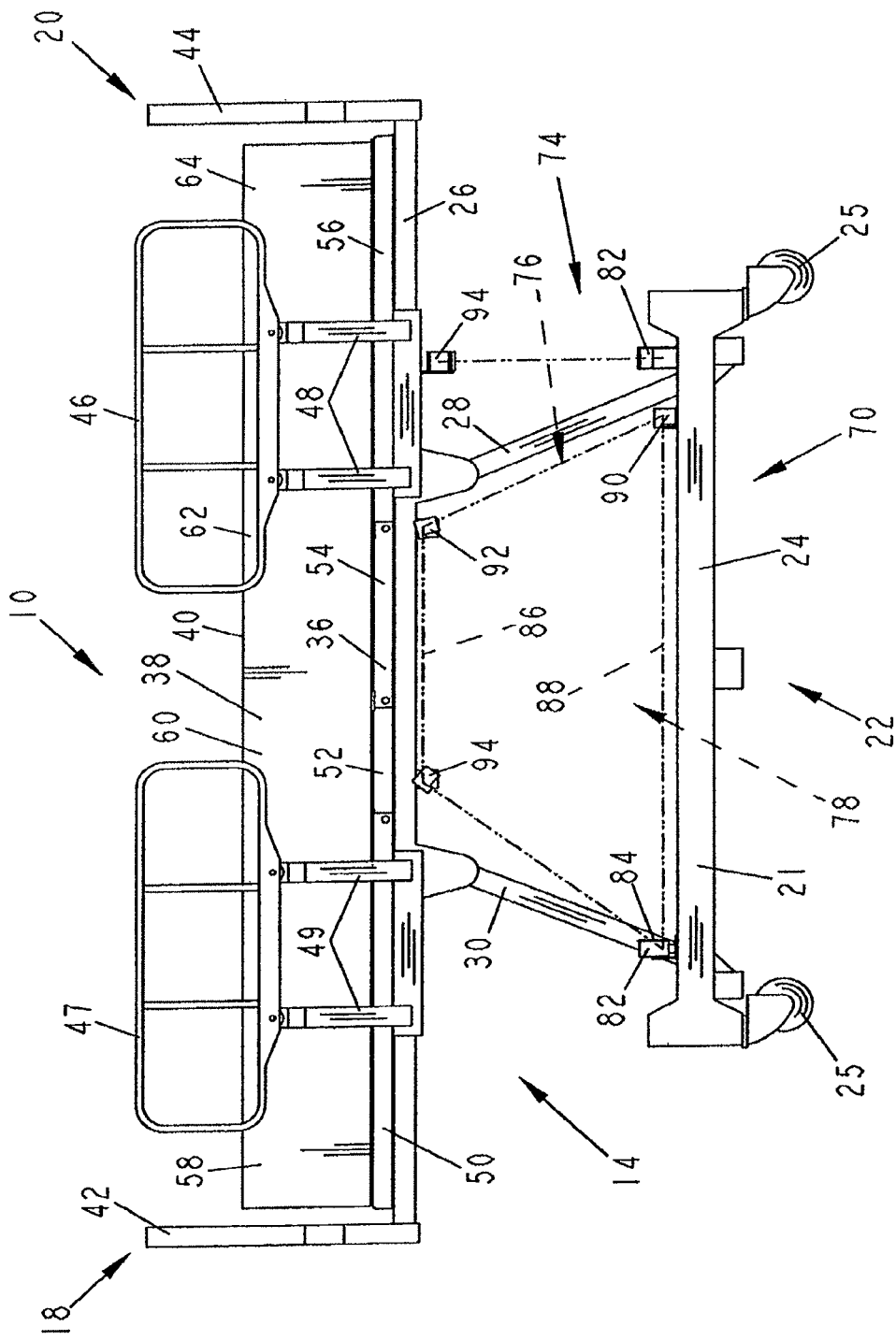
FIG. 2 is a side elevational view of the hospital bed of FIG. 1, the opposite side elevational view being a mirror image thereof.
Figure 3:
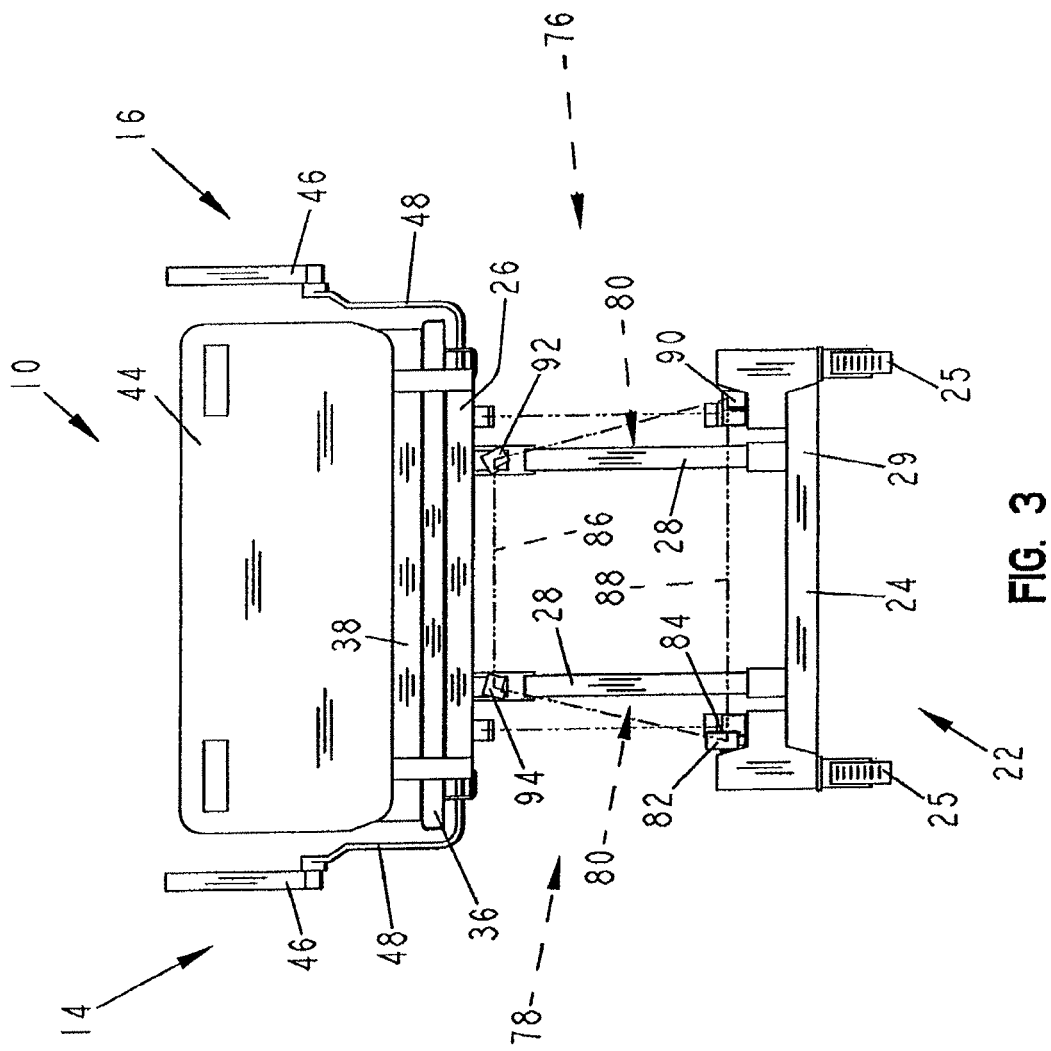
FIG. 3 is a foot end view of the hospital bed of FIG. 1.

Referring initially to FIGS. 1-3, a hospital bed 10 is illustrated as including the obstacle detection device 12 of the present invention. The hospital bed 10 includes opposing right and left longitudinal side edges 14 and 16 extending between a head end 18 and a foot end 20. In the following description, the phrases "right side" and "left side" will be utilized to denote the relative location of an object positioned to lie nearest the right side edge 14 and left side edge 16, respectively, of the bed 10. The phrase "head end" will be utilized to denote the relative location of an object positioned to lie nearest the head end 18 of the hospital bed 10. Likewise, the phrase "foot end" will be used to denote the proximate location of a referenced object positioned to lie nearest the foot end 20 of the hospital bed 10.

The hospital bed 10 includes a base module 22 having a base frame 24 supported by conventional casters 25 which provide mobility to the bed 10. The base frame 24 includes a right side member 21 and a left side member 23 connected by a foot end cross member 29 and a head end cross member 31. An intermediate or elevating frame 26 is coupled to the base frame 24 by first and second pairs of lift arms 28 and 30 in a manner providing for vertical movement of the elevating frame 26 relative to the base frame 24. An articulating deck 36 is supported for movement relative to the elevating frame 26. A mattress 38 is carried by the articulating deck 36 and provides a sleeping or patient support surface 40 configured to receive a patient.

A headboard 42 is illustratively supported by the elevating frame 26 proximate the head end 18 of the bed 10 while a footboard 44 is supported by the elevating frame 26 proximate the foot end 20 of the bed. It should be appreciated that the headboard 42 and the footboard 44 may alternatively be coupled to the base frame 24. Conventional first and second siderails 46 and 47 are provided proximate the longitudinal side edges 14 and 16 of the bed 10. The first siderails 46 are positioned proximate the foot end 20 of the bed 10, while the second siderails 47 are positioned proximate the head end 18 of the bed 10. A pair of arms 48 and 49 couple each of the siderails 46 and 47 to the articulating deck 36 in a manner providing for relative vertical movement therebetween.

The articulating deck 36 includes a head section 50, a seat section 52, a thigh section 54, and a foot section 56. Illustratively, the first siderails 46 are supported by the foot section 56, while the second siderails 47 are supported by the head section 50. As such, it should be appreciated that the siderails 46 and 47 move relative to each other as the foot section 56 and the head section 50 of the articulating deck 36 move relative to each other. The mattress 38 rests on the articulating deck 36 and includes a head portion 58, a seat portion 60, a thigh portion 62, and a foot portion 64, each of which generally correspond to the like-named portions of the deck 36, and each of which is generally associated with the head, seat, thighs, and feet of a patient supported on the surface 40. Details of the articulating deck 36 are of conventional design and may comprise those of the type disclosed in U.S. Pat. No. 6,336,235 to Ruehl, which is assigned to the assignee of the present invention and which is expressly incorporated by reference herein.

The lift arms 28 and 30 are operably connected to a drive or lifting device 66 (FIG. 4) for causing the vertical movement of the elevating frame 26 relative to the base frame 24. More particularly, the elevating frame 26 is configured to move vertically between a raised position (FIG. 5) and a lowered position (FIG. 6). A plurality of intermediate positions (FIG. 7) are available for the elevating frame 26 between the raised position and the lowered position. The lifting device 66 may comprise a conventional mechanism of the type disclosed in U.S. Pat. No. 3,958,383 to Adams et al. or U.S. Pat. No. 6,336,235 to Ruehl, both of which are assigned to the assignee of the present invention and which are expressly incorporated by reference herein.

With reference now to FIGS. 1-4, the obstacle detection device 12 of the present invention includes a first or right side detection unit 70, associated with the right side longitudinal edge 14 of the hospital bed 10, a second or left side detection unit 72 associated with the left longitudinal side edge 16 of the bed 10, and a third or foot end detection unit 74 associated with the foot end 20 of the bed 10. The right side detection unit 70 is configured to generate a first optical curtain 76 (FIG. 2) while the left side detection unit 72 is configured to generate a second optical curtain 78 substantially identical to the first optical curtain 76. Likewise, the foot end detection unit 74 is configured to generate a third optical curtain 80 (FIG. 3). A fourth or head end detection unit (not shown) substantially identical to the foot end detection unit 74 may likewise be provided adjacent the head end 18 of the bed 10 for generating a fourth optical curtain (not shown) similar to the optical curtains 76, 78, and 80. Illustratively, each detection unit 70, 72, and 74 includes an emitter 82 coupled to the base frame 24. The emitter 82 illustratively comprises a light source, such as an infrared (IR) light emitting diode (LED). The light emitting diode may be empirically selected based upon dimensions and operating conditions of the bed 10.

Illustratively, an emitting diode Model No. SFH41SU available from OSRAM Opto Semiconductors of San Jose, Calif., may be utilized. However, it should be appreciated that other conventional emitters, including ultrasonic, radar, and microwave may be substituted for the infrared emitters. A beam shaping lens 84 is positioned adjacent to each emitter 82 for converting or shaping a beam of light emitted from the emitter 82 into the respective optical curtain 76, 78, 80. The beam shaping lens 84 may comprise a fresnel lens of the type well-known in the art. Illustratively, Model No. H43796 available from Edmund Scientific of Tonawanda, N.Y., may be utilized. It should be noted that a plurality of emitters 82 may be utilized to form each respective optical curtain 76, 78, 80, thereby eliminating the beam shaping lens 84.

The emitter 82 in combination with the lens 84 directs light a predetermined distance from the emitter 82 thereby minimizing spillover to adjacent equipment. Moreover, each respective emitter 82 and lens 84 define a perimeter including a predetermined width and height for the optical curtains 76, 78, and 80. The predetermined height is defined to extend from an upper edge 86 to a lower edge 88 intermediate the base frame 24 and the elevating frame 26. Illustratively, the predetermined height is equal to the distance between the base frame 24 and the elevating frame 26 when the elevating frame 26 is in its uppermost position (FIG. 5) as defined by the lifting device 66.

A plurality of detectors 90, 92, 94 are associated with each emitter 82 and are configured to receive or detect the respective optical curtain 76, 78, and 80. The detectors 90, 92, and 94 are identified as Detector A, Detector B, and Detector C, respectively in FIG. 4. Moreover, each optical curtain 76, 78, 80 is illustratively formed by a plurality of individual wireless infrared signals 96 (FIGS. 5-8) emitting from the emitter 82 and detectable by the detectors 90, 92, 94. Illustratively, Opto Sensor Model No. BPW-34F from OSRAM Opto-Semiconductors of San Jose, Calif., may be used for detectors 90, 92, 94. However, it should be noted that other similar detectors may be readily substituted therefore. Moreover, as detailed below, detectors which are operable independently of an emitter, such as proximity sensors or cameras, may be substituted for the combined infrared detectors 90, 92, 94 and emitters 82.

Figure 4:
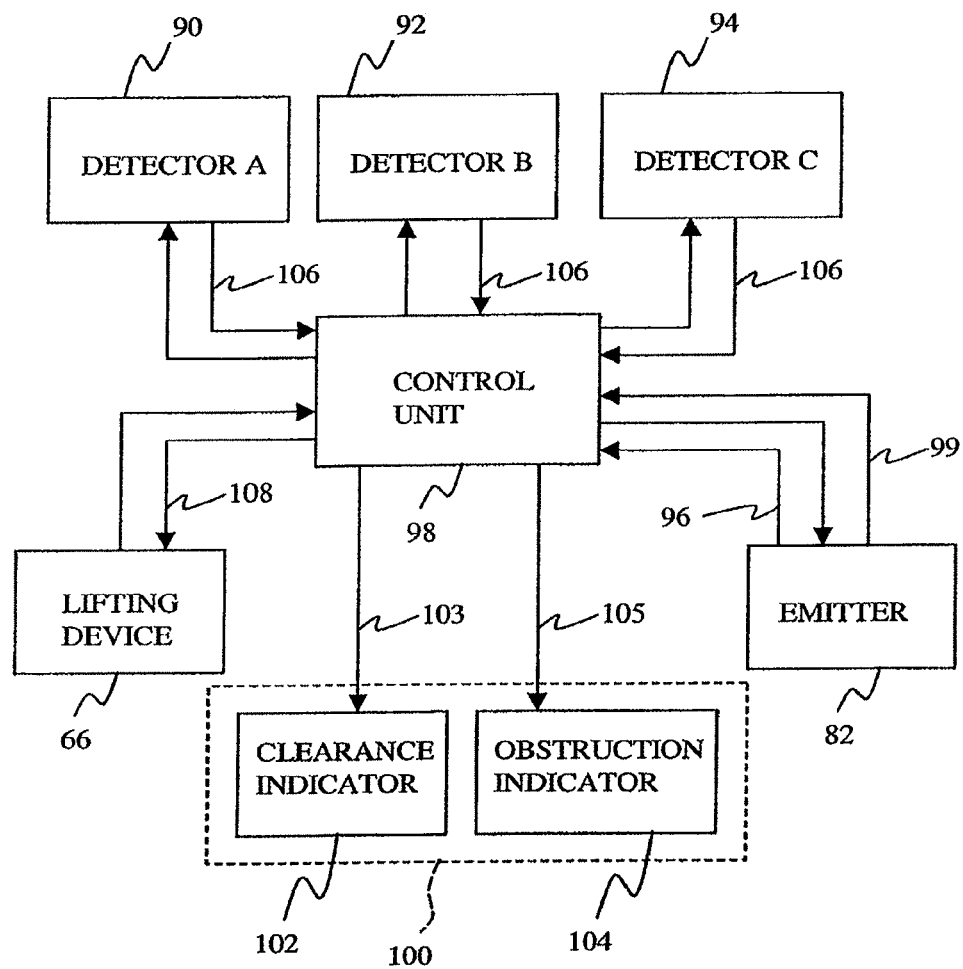
FIG. 4 is a block diagram representation of the obstacle detection device of FIG. 1.

Referring further to FIG. 4, a control unit 98 is provided in communication with each emitter 82 and detector 90, 92, 94. In one embodiment of the invention, each emitter 82 transmits randomly modulated wireless infrared light rays or signals 96 to form a respective optical curtain 76, 78, 80. A source modulation or verification signal 99 is then transmitted through a conventional communication link, such as hard wires (not shown) disposed within the bed base frame 24, to the control unit 98. If the intensity, spectrum or modulation of the received wireless signal 96 at the detector 90, 92, 94 does not match the verification signal 99, the control unit 98 inhibits movement of the bed 10 by the lifting device 66. As such, the verification signal 99 prevents external light sources, such as room lights or sunlight, from interfering with the operation of the obstacle detection device 12.

An indicator 100 may be supported by the hospital bed 10 for providing an indication of the detection of the optical curtain 76, 78, 80 by the detectors 90, 92, 94. More particularly, the indicator 100 may include a clearance indicator, illustratively in the form of a green light 102, which is activated by a clearance signal 103 supplied by the control unit 98 to provide an indication of a clear detection path between the emitter 82 and the detectors 90, 92, 94. An obstruction indicator, illustratively in the form of a red light 104, may be provided to indicate a failure of one of the detectors 90, 92, 94 to receive the appropriate wireless signal 96 of the optical curtains 76, 78, 80. The obstruction indicator 104 is activated by an obstruction signal 105 supplied by the control unit 98. It should be appreciated that the indicator 100 may comprise a single bi-color red/green status indicator. Alternatively, other indicators, such as an audible alarm or any other device which may provide an indication of the presence of an obstacle in the detection path, may be readily substituted for the obstruction indicator light 104.

Figure 7:
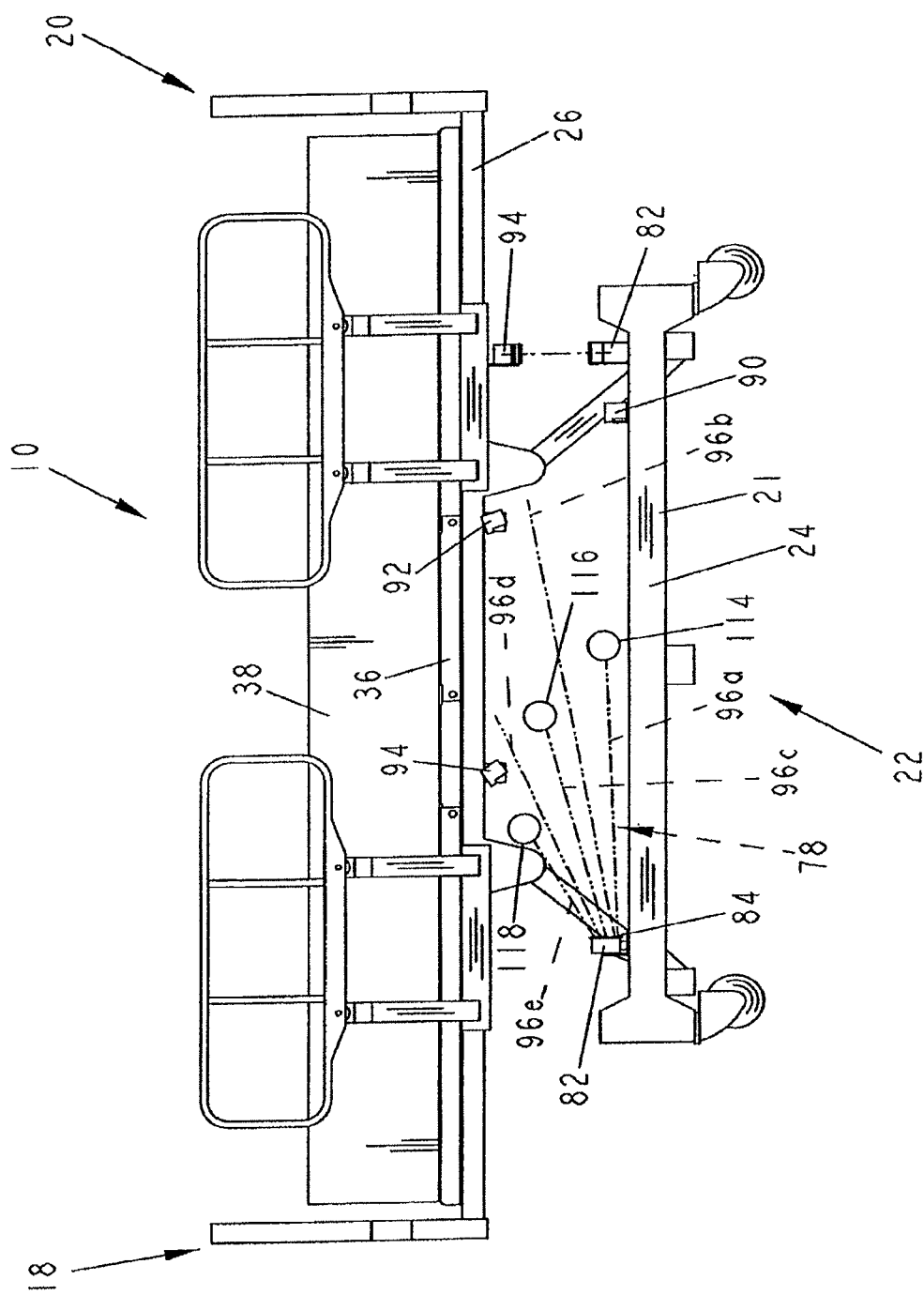
FIG. 7 is a side elevational view in partial schematic similar to FIG. 5, illustrating the bed in an intermediate position.
Figure 8:
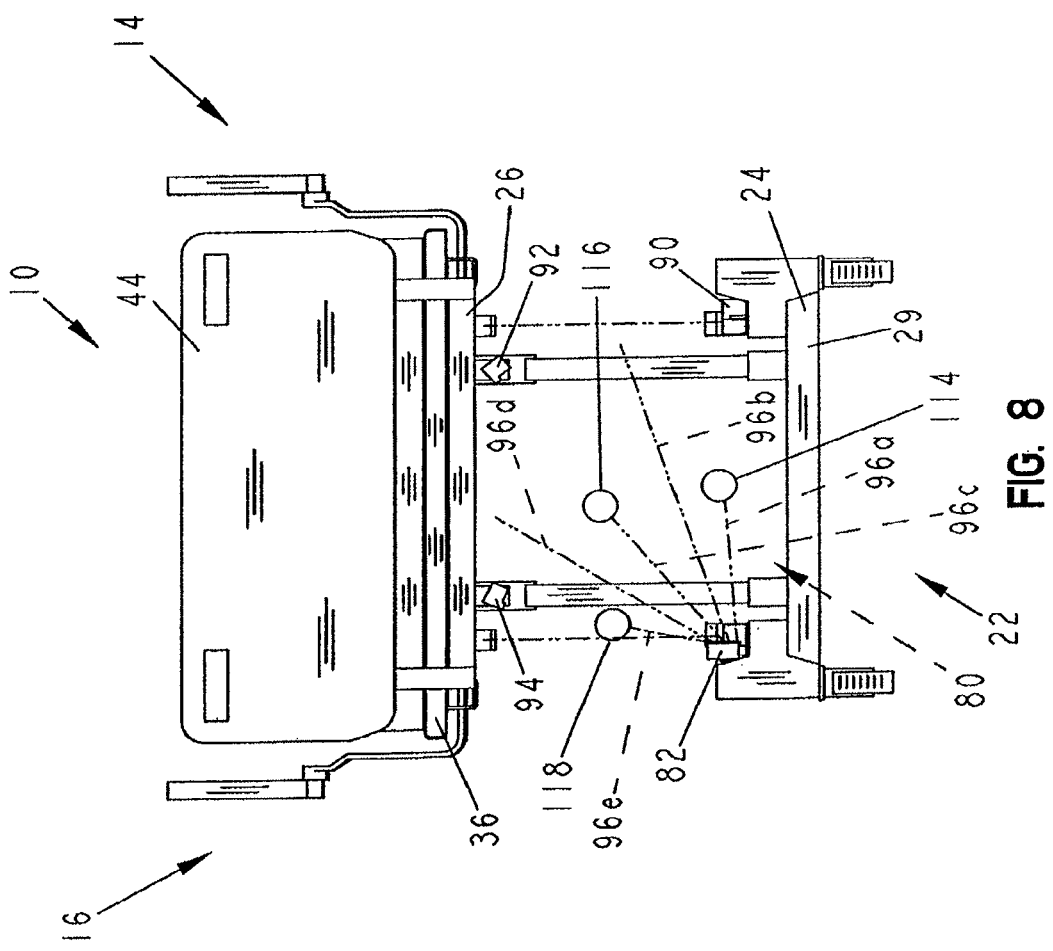
FIG. 8 is a foot end view in partial schematic of the hospital bed of FIG. 5, illustrating the bed in a fully raised position and with potential obstacles positioned in detection paths of the various receivers.
Figure 9:
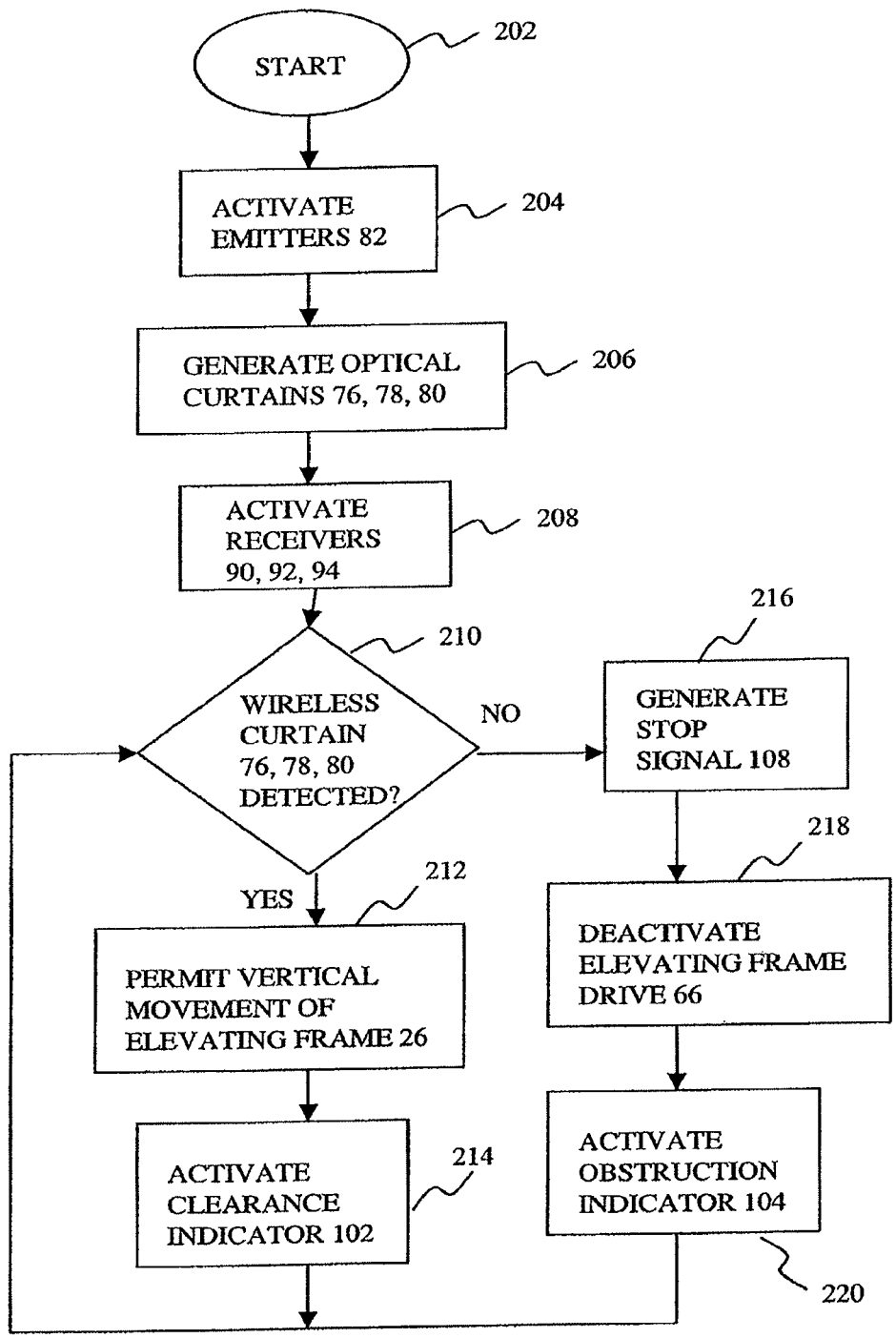
FIG. 9 is a flow chart illustrating the method operation associated with the obstacle detection device of FIG. 1.

With reference to FIGS. 5-9, the operation of the obstacle detection device 12 of the present invention is described in greater detail. As illustrated in FIG. 9, the process begins at block 202 upon activation of the obstacle detection device 12. The process continues to block 204 where the respective emitters 82 are activated. At block 206, the optical curtains 76, 78, 80 are formed by passing a light beam containing rays or signals 96 produced by the respective emitters 82 through the associated beam shaping lenses 84.

Continuing at block 208, the respective receivers 90, 92, 94 are activated. The receivers 90, 92, 94 determine whether the respective wireless curtain 76, 78, 80 is detected. If the curtain 76, 78, 80 is detected, then the process continues to block 212 where vertical movement of the elevating frame is permitted by the control unit 98. At block 214, the clearance indicator 102 is activated in response to the clearance signal 103 supplied by the control unit 98.

If one of the wireless curtain 76, 78, 80 is not detected by the respective detectors 90, 92, 94 at block 210, then the respective detector 90, 92, 94 sends an interruption signal 106 to the control unit 98. The process continues to block 216 where the control unit 98 generates a stop signal 108. At block 218, the elevating frame lifting device 66 is deactivated in response to the stop signal 108. At block 220, the obstruction indicator 104 is activated in response to the obstruction signal 105 supplied by the control unit 98.

Figure 5:
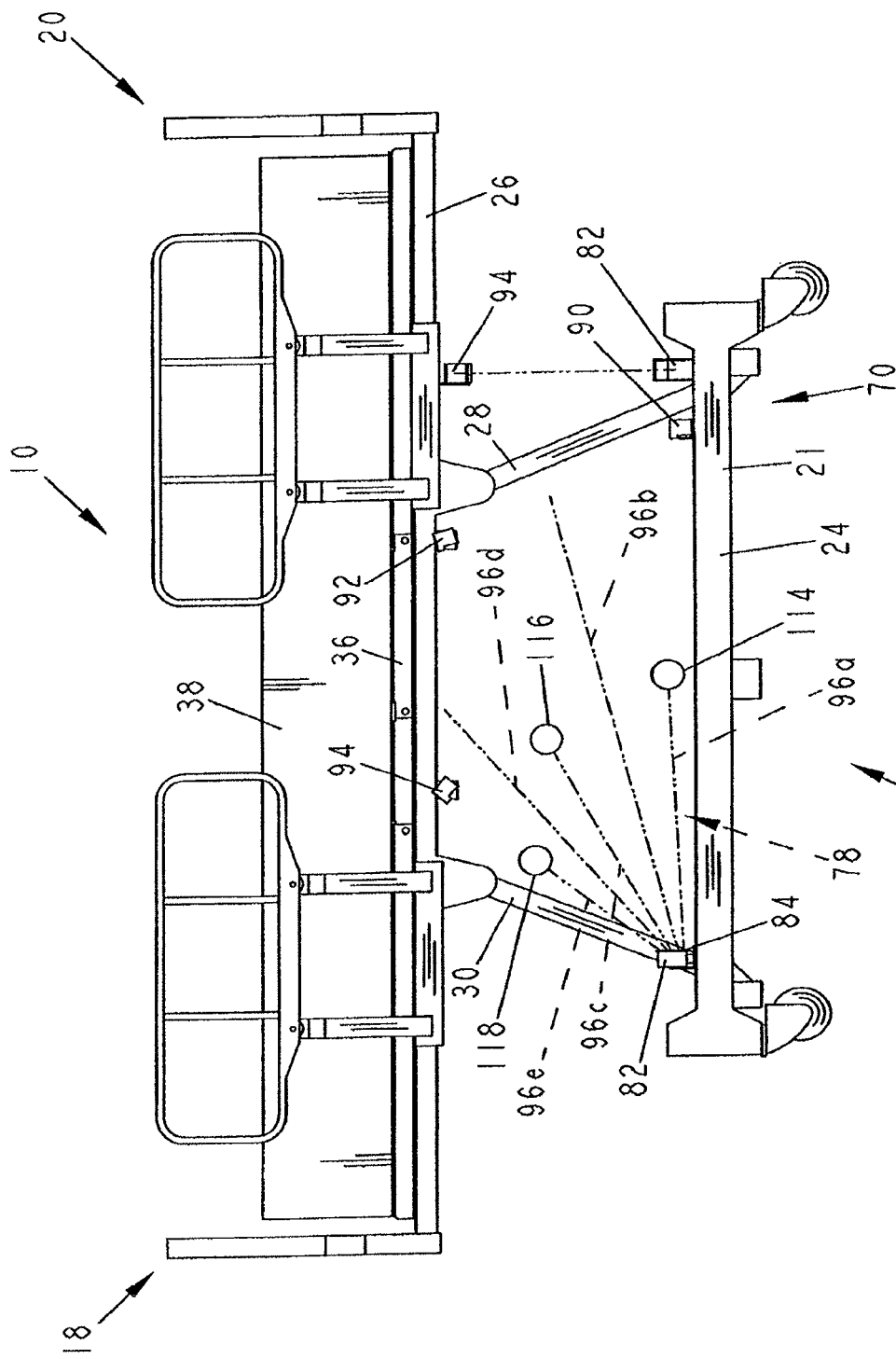
FIG. 5 is a side elevational view in partial schematic of the hospital bed of FIG. 1, illustrating the bed in a fully raised position and with potential obstacles positioned in detection paths of the various receivers.
Figure 6:
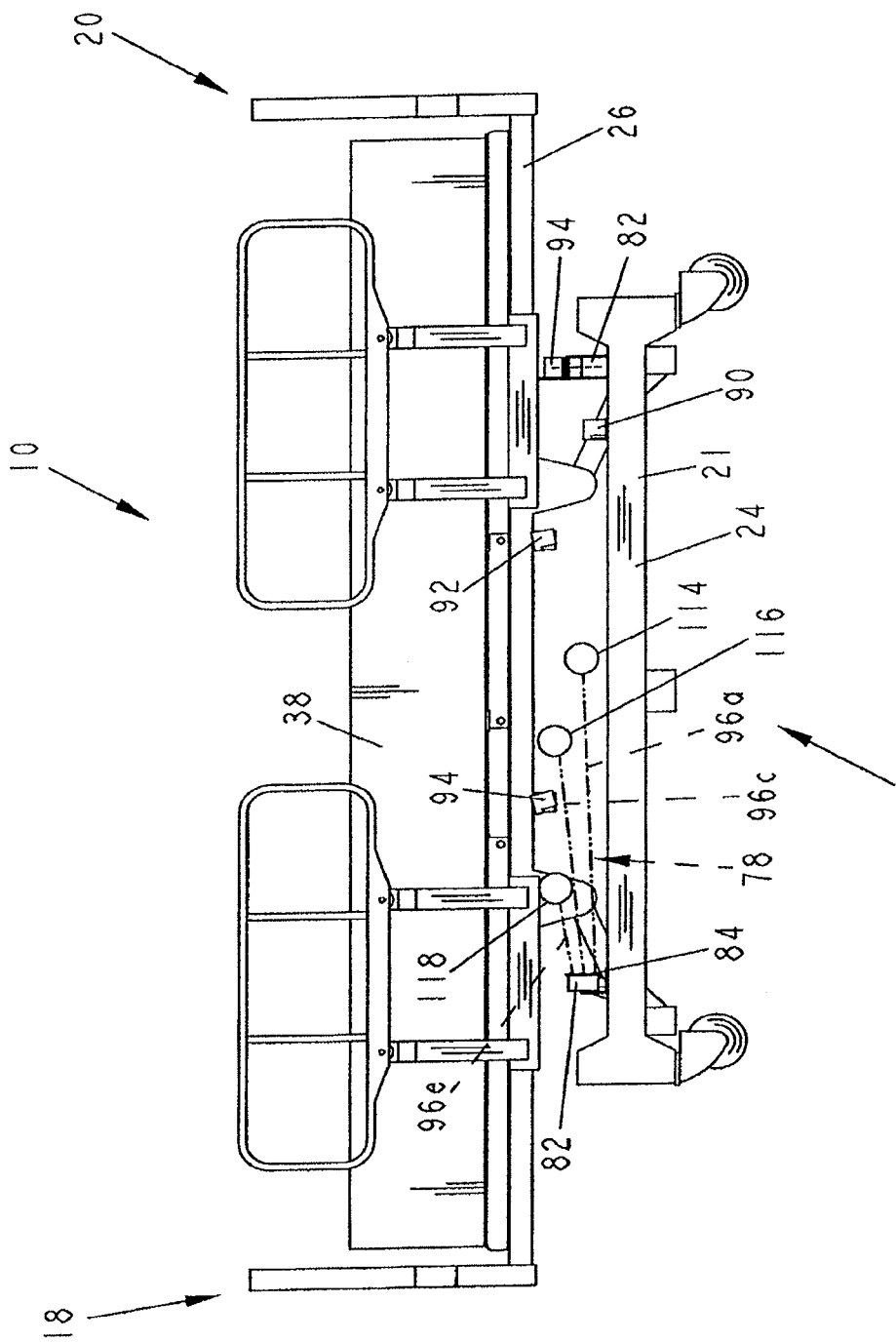
FIG. 6 is a side elevational view in partial schematic similar to FIG. 5, illustrating the bed in a lowered position.

FIG. 5 illustrates the hospital bed 10 in a fully raised position. Moreover, the elevating frame 26 is raised to its uppermost position by the lifting device 66 coupled 5 to the lift arms 28, 30. FIG. 6, in turn, illustrates the elevating frame 26 of the hospital bed 10 in its lowermost position wherein the elevating frame 26 is lowered to its position nearest the base frame 24 through operation of the lifting device 66 and the lift arms 28, 30, 32, 34. FIG. 7 illustrates the hospital bed 10 with the elevating frame 26 in a intermediate position between the uppermost position of FIG. 5 to the lowermost position of FIG. 6.

It should be noted that the lifting device 66 may be provided with position sensors (not shown) configured to provide feedback position signals to the control unit 98 providing an indication of the relative vertical position of the elevating frame 26. Such position sensors are well-known in the art and may be utilized with the obstacle detection device 12 of the present invention to prevent the elevating frame 26 from moving outside of the range of the optical curtains 76, 78 and 80.

As noted above, the receivers 90, 92, 94 for each optical curtain 76, 78, 80 are configured to receive wireless signals 96 making up or forming the respective curtains 76, 78, 80. The wireless signals 96 travel along a plurality of detection paths from the emitter 82 to the receivers 90, 92, 94. Representative wireless signals 96a, 96b, 96c, 96d and 96e are illustrated in FIGS. 5 and 8. Potential obstacles are represented by reference numerals 114, 116 and 118 in FIG. 5 and are placed within the respective detection paths of signals 96a, 96c, and 96e. The obstacles 114, 116, 118 prevent the wireless signals 96a, 96c, and 96e of the optical curtains 78 and 80 from reaching the respective detectors 90, 92, 94. The obstacles 114, 116, 118 may comprise a person, medical instruments or any other object found within a hospital room.

Figure 10:
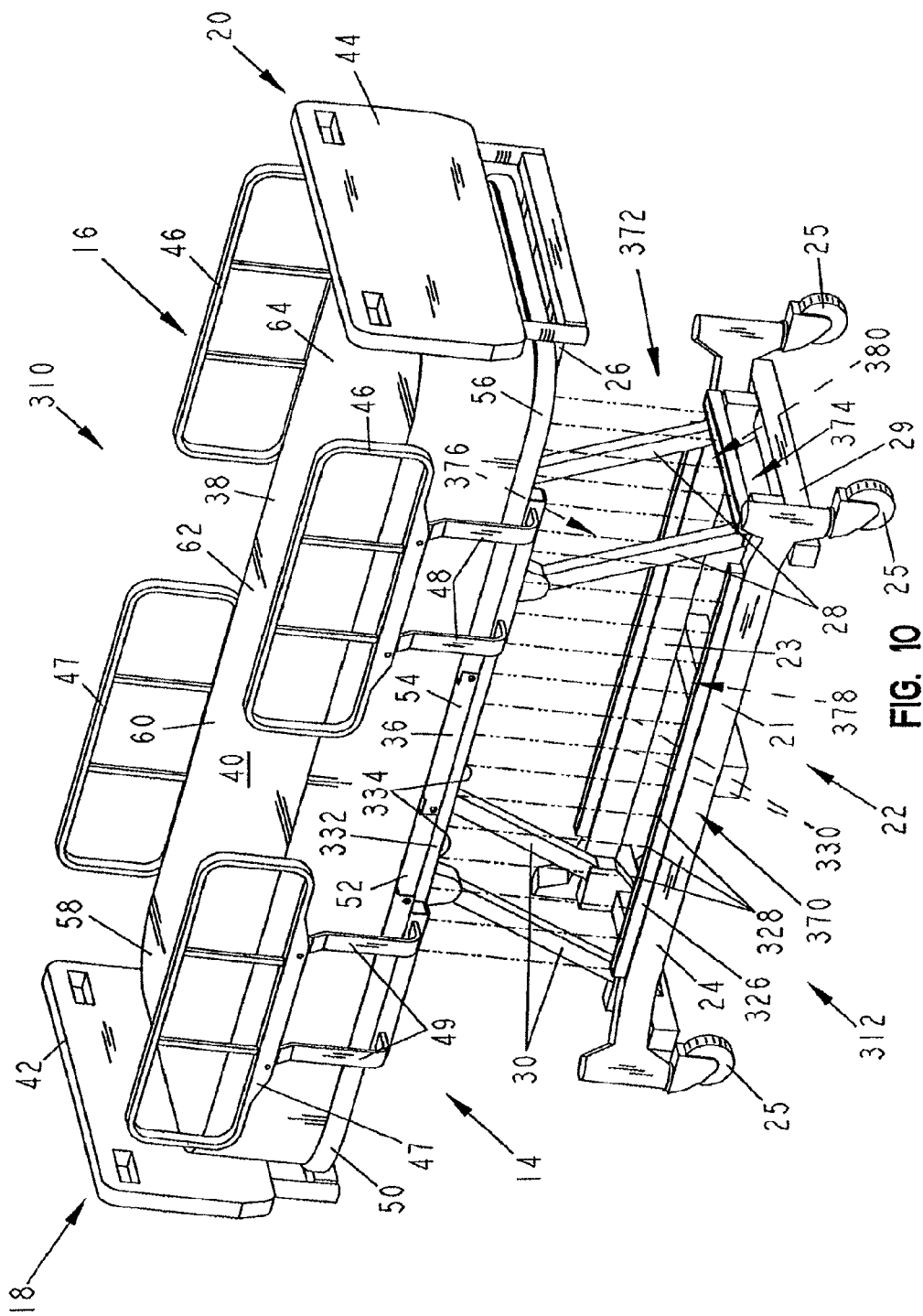
FIG. 10 is a perspective view of a hospital bed incorporating a further illustrative embodiment of the obstacle detection device of the present invention.
Figure 11:
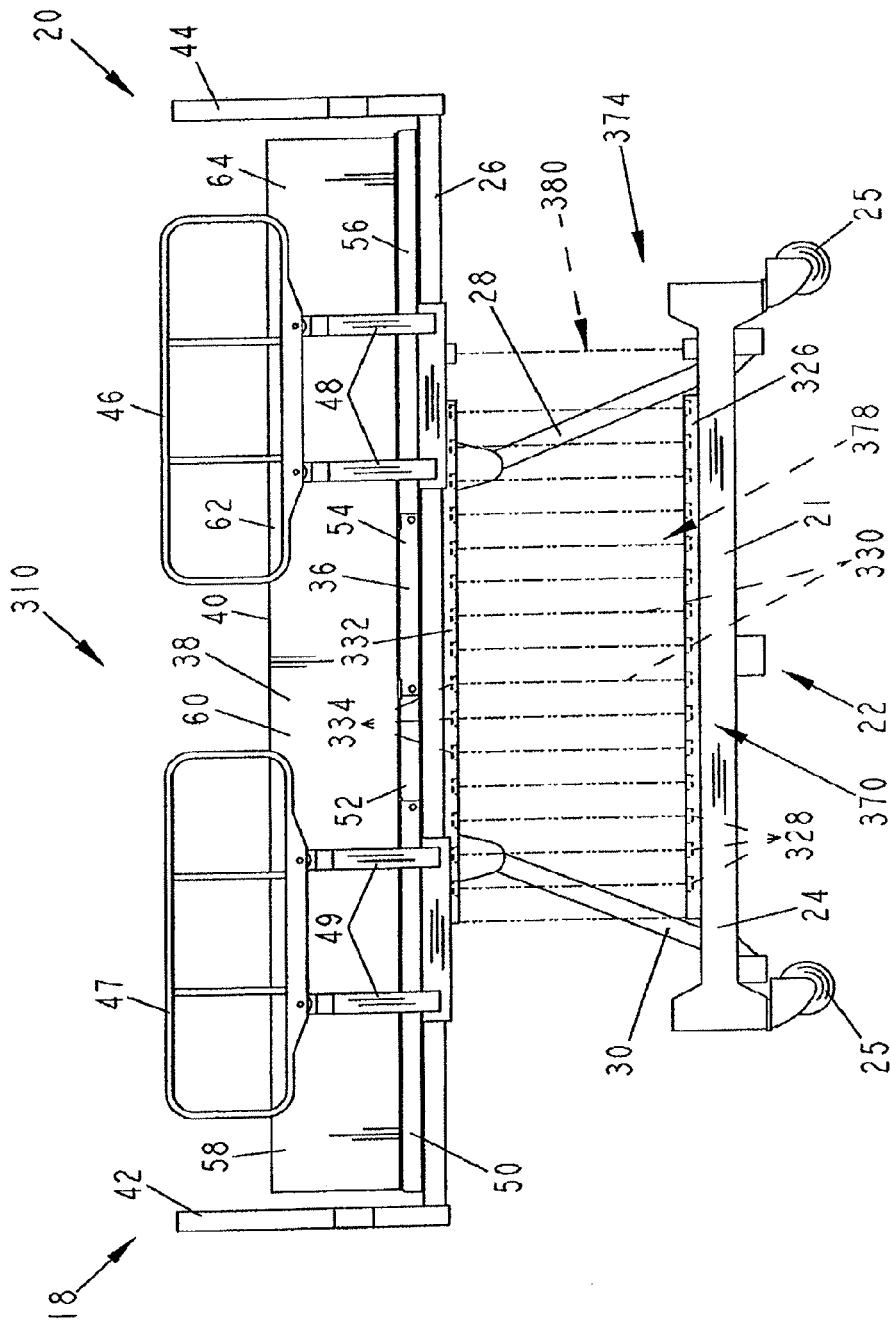
FIG. 11 is a side elevational view of the hospital bed of FIG. 10, the opposite side elevational view being a mirror image thereof.

FIGS. 10 and 11 illustrate a hospital bed 310 including an alternative embodiment obstacle detection device 312 of the present invention. The obstacle detection device 312 includes a first or right side detection unit 370 associated with the right longitudinal side edge 14 of the hospital bed 310, a second or left side detection unit 372 associated with the left longitudinal side edge 16 of the bed 310, and a third or foot end detection unit 374 associated with the foot end 20 of the bed 310. The right side detection unit 370 is configured to generate a first optical curtain 376, while the left side detection unit 372 is configured to generate a second optical curtain 378. Likewise, the foot end detection unit 374 is configured to generate a third optical curtain 380. A fourth or head end detection unit (not shown) may be provided adjacent the head end 18 of the bed 310 for generating a fourth optical curtain (not shown) similar to the optical curtains 376, 378, and 380.

Illustratively, each detection unit 370, 372, and 374 of the obstacle detection device 312 includes a first or lower support 326 including a plurality of spaced apart emitters 328. Each emitter 328 preferably comprises a self-contained infrared light-emitting diode. The emitters produce a beam of light 330 upwardly toward the elevating frame of the bed 10. As illustrated in FIGS. 10 and 11, each beam of light 330 is discrete and spaced apart from adjacent beams of light 330. Collectively, the plurality of beams of light 330 define the respective optical curtains 376, 378, and 380.

Each detection unit 370, 372, and 374 of the optical detection device 312 further includes a second or upper support 332 including a plurality of detectors 334. Each detector 334 is associated with one of the emitters 328 and is configured to receive or detect the respective light beam 330 defining the optical curtains 376, 378, and 380.

In a manner similar to that detailed above, if an obstacle is located in the optical curtain 376, 378, 380 between one of the emitters 328 and detectors 334, such that one of the light beams 330 is interrupted, then the control unit 98 prevents the lifting device 66 from vertically moving the elevating frame 26.

It should be noted that the optical curtains 376, 378, and 380 of the obstacle detection device 312 require that the light beams 330 be accurately aligned between the emitters 328 and the detectors 334 throughout the full path of travel of the elevating frame 26. It may be appreciated, non-linear movement of the elevating frame 26 relative to the base frame 24 may cause the respective emitters 328 and detectors 334 to become mis-aligned, thereby resulting in a signal to the control unit 98 that an obstacle is positioned within the optical curtain 376, 378, 380. Such false optical detection signals are less likely to occur using the earlier embodiment having substantially uniform optical curtains 76, 78, 80.

The individual detection units 370, 372, and 374 of the obstacle detection device 312 may comprise the EASY-GUARD™ grid system available from Banner Engineering Corp. of Minneapolis, Minn. However, it should be appreciated that other similar devices may be substituted therefore.

Figure 12:
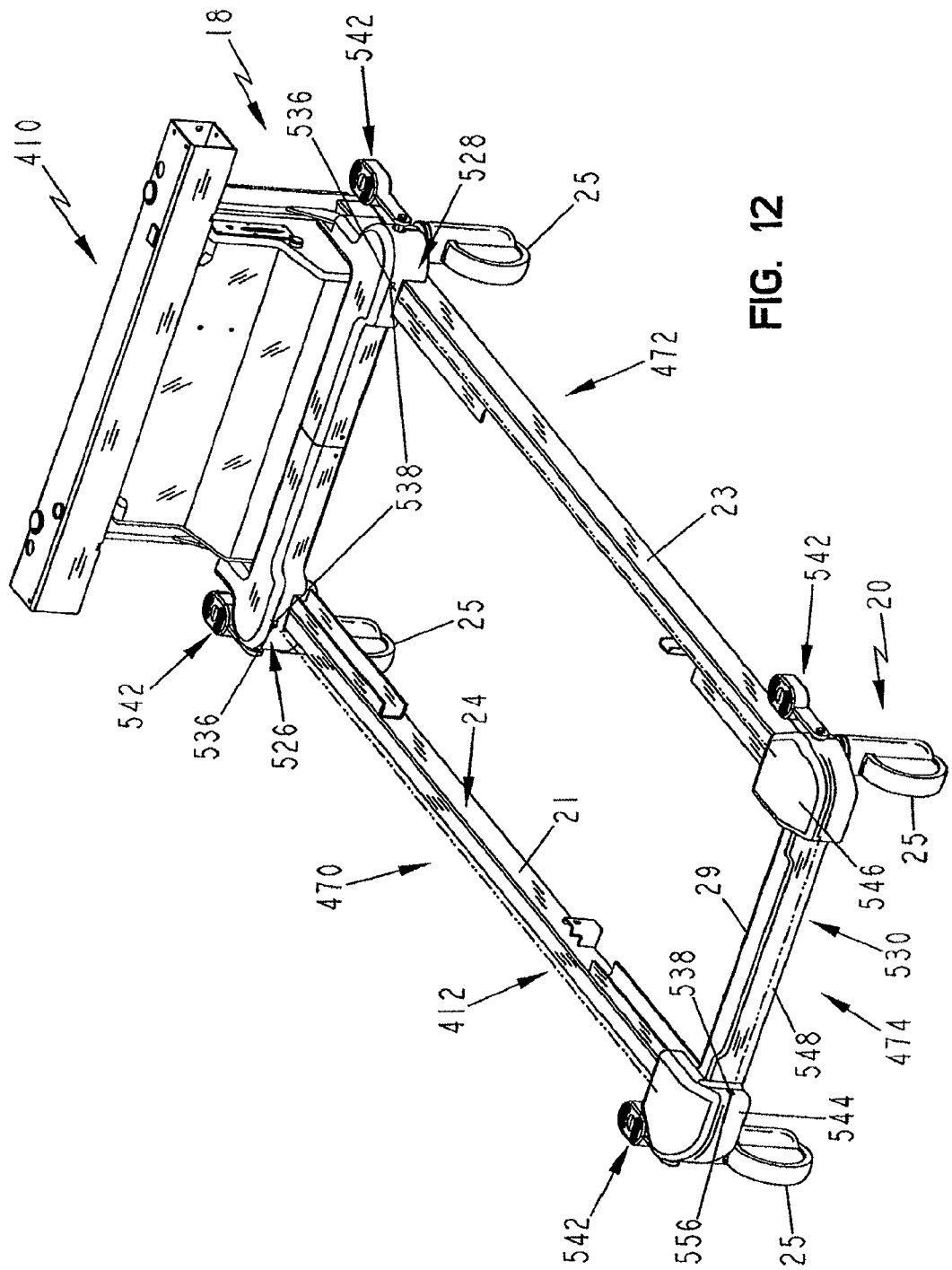
FIG. 12 is a perspective view of a hospital bed, with certain components removed for clarity, incorporating a further illustrative embodiment obstacle detection device of the present invention.
Figure 13:
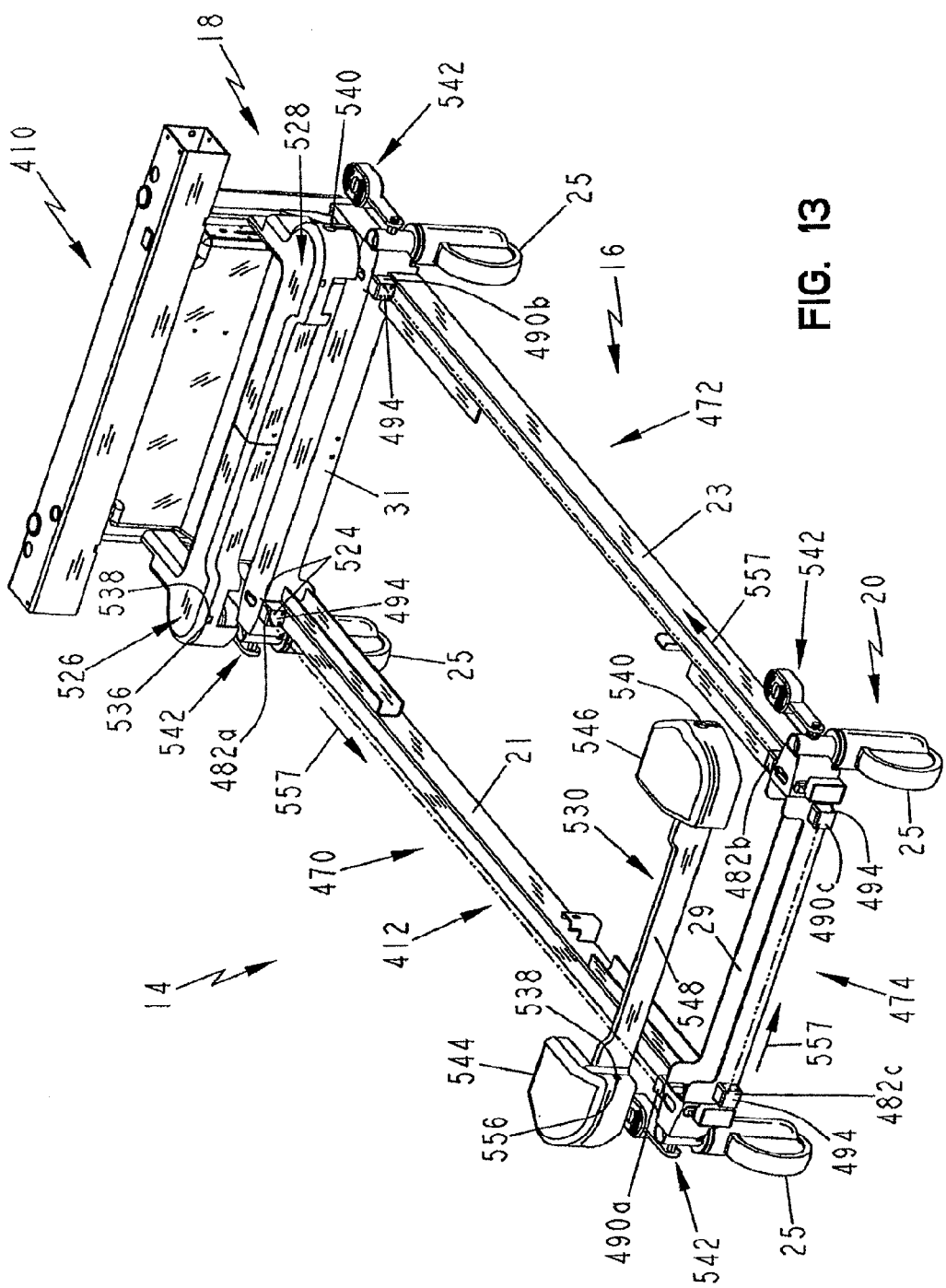
FIG. 13 is a partially exploded perspective view similar to FIG. 12, with the frame covers raised to illustrate the emitters and the detectors of the obstacle detection device.
Figure 14:
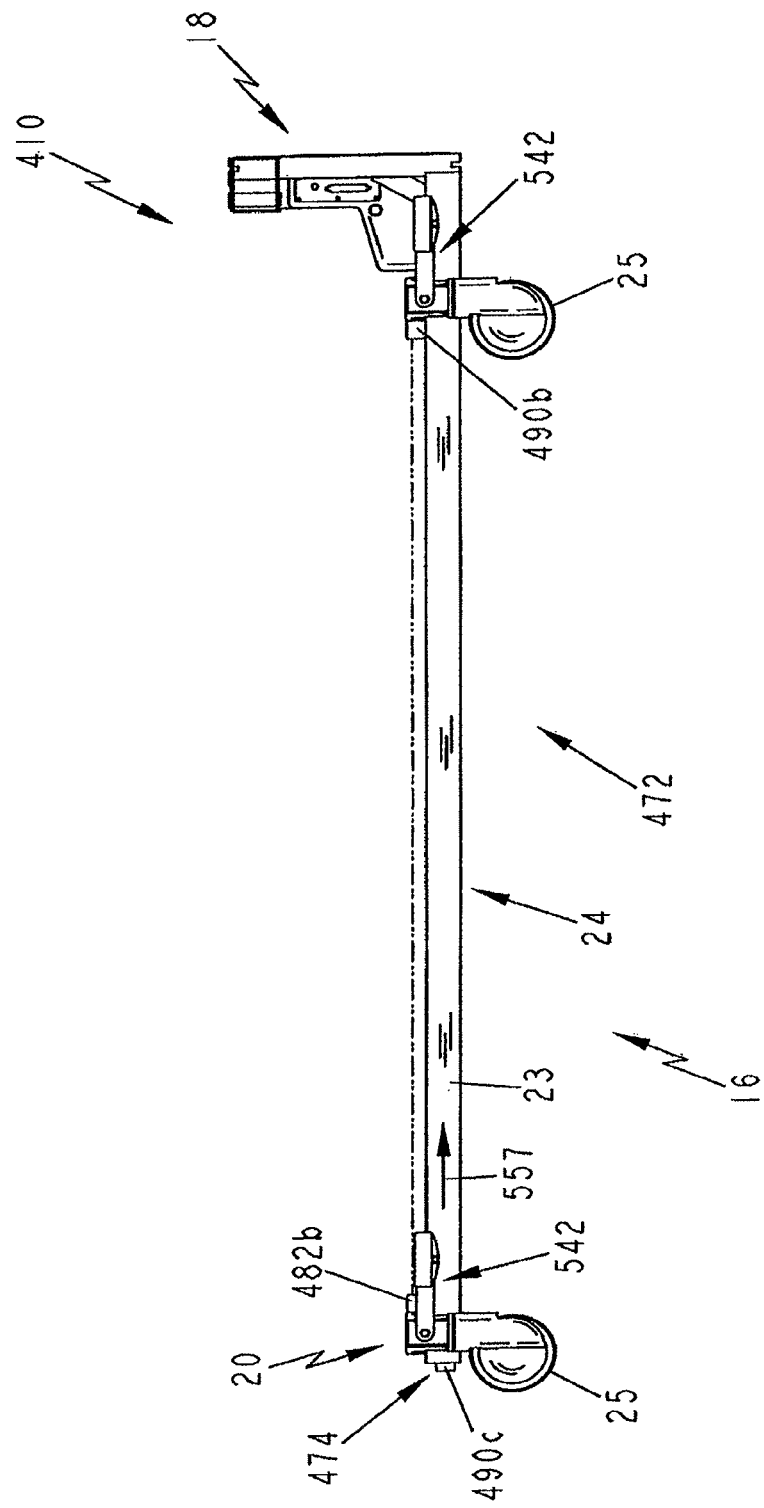
FIG. 14 is a side elevational view of the hospital bed of FIG. 12, with the frame covers removed for clarity, the opposite side elevational view being a mirror image thereof.
Figure 15:
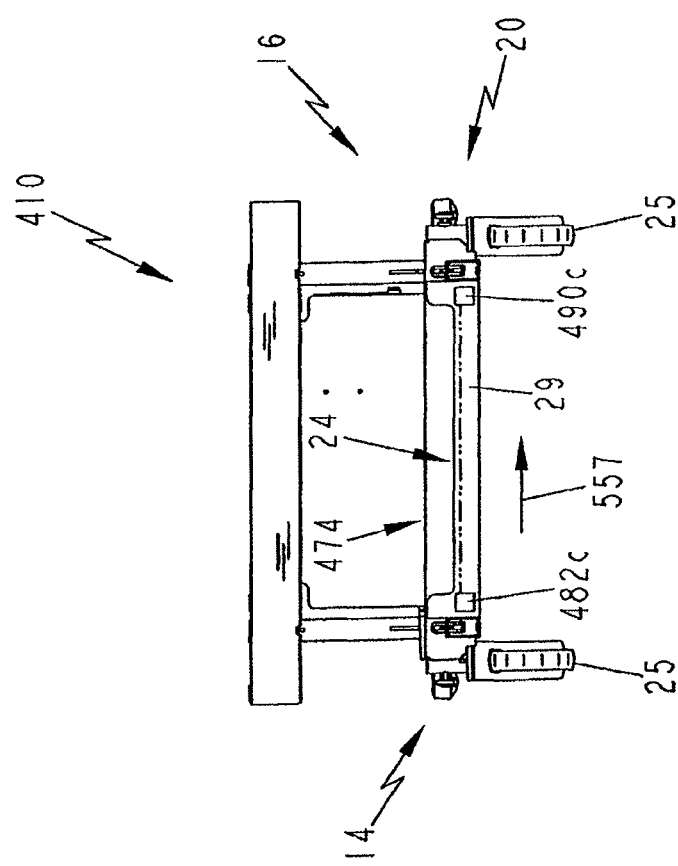
FIG. 15 is a foot end view of the hospital bed of FIG. 12, with the frame covers removed for clarity.
Figure 16:
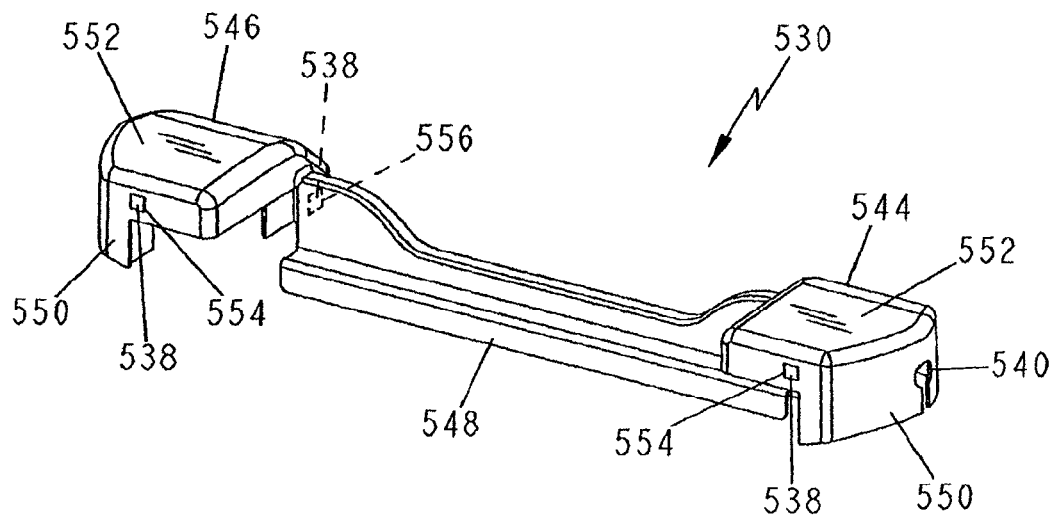
FIG. 16 is a rear perspective view of the foot end frame cover of the hospital bed of FIG. 12.
Figure 17:
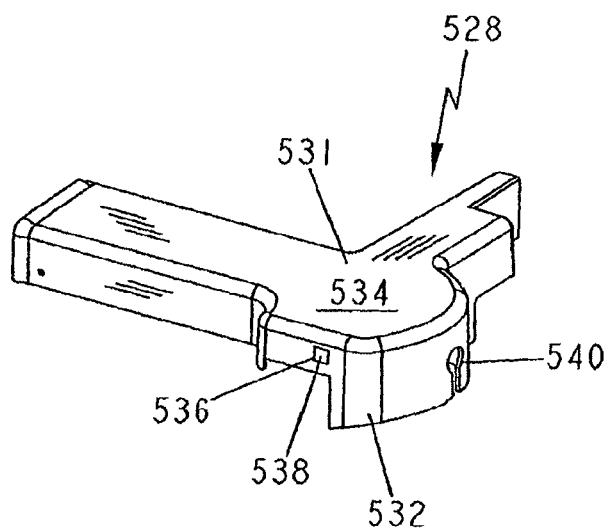
FIG. 17 is a perspective view of the left side head end frame cover of the hospital bed of FIG. 12, the right side head end frame cover being a mirror image thereof.
Figure 18:
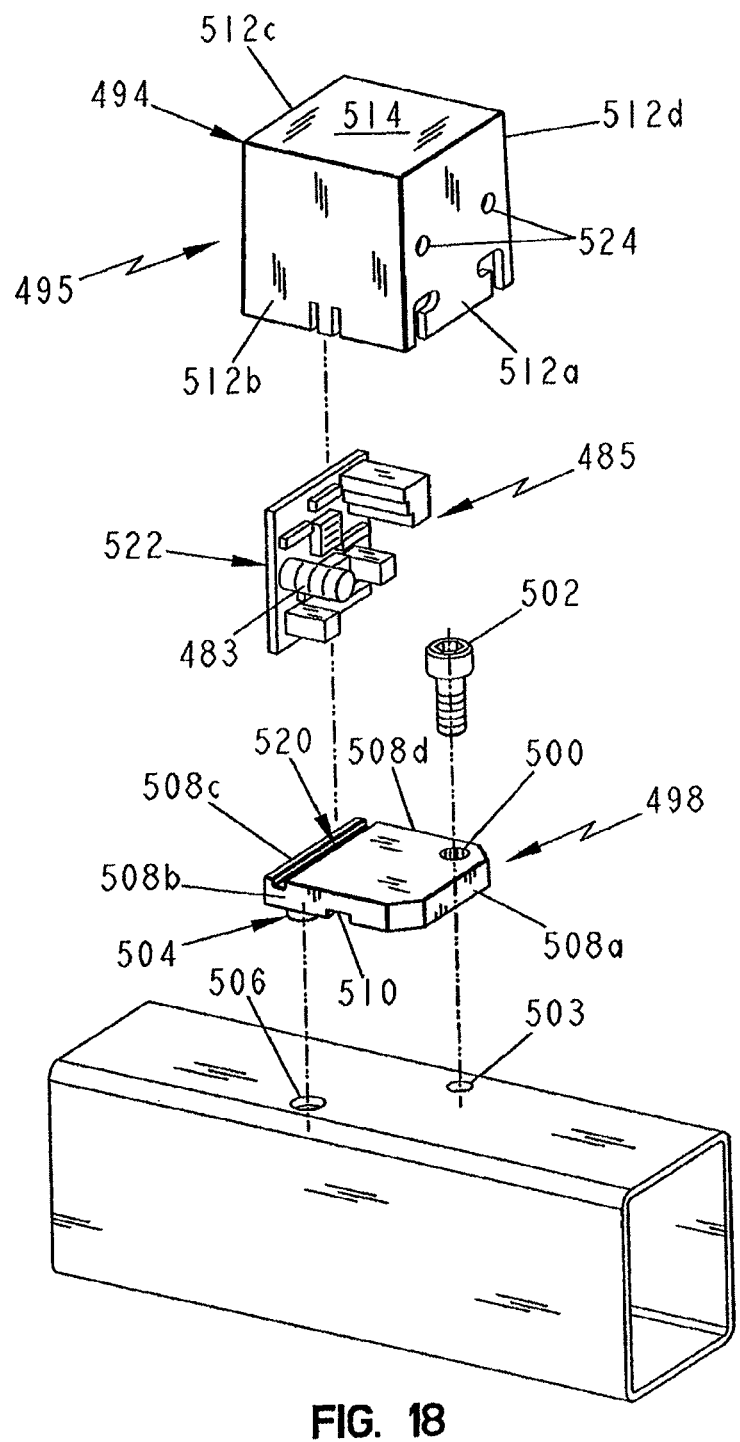
FIG. 18 is an exploded perspective view of a housing of the obstacle detection device of FIG. 12.
Figure 19:
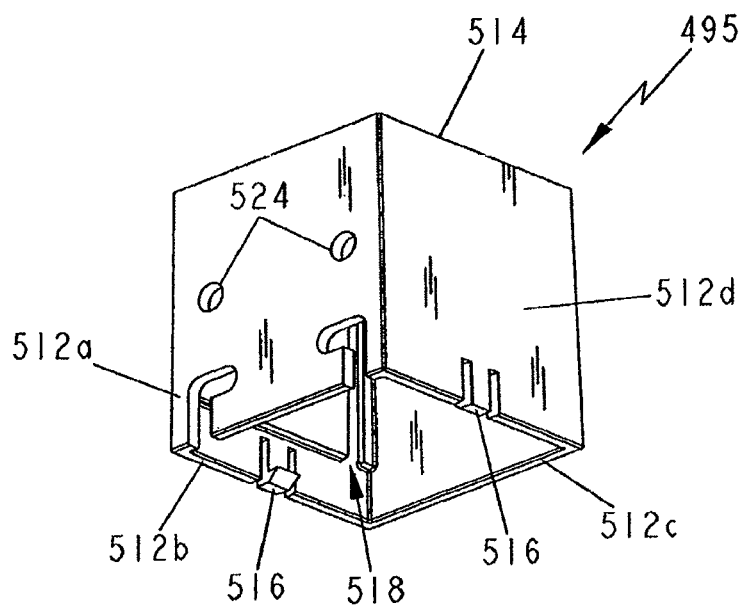
FIG. 19 is a perspective view of a cover of the housing of FIG. 18.
Figure 20:
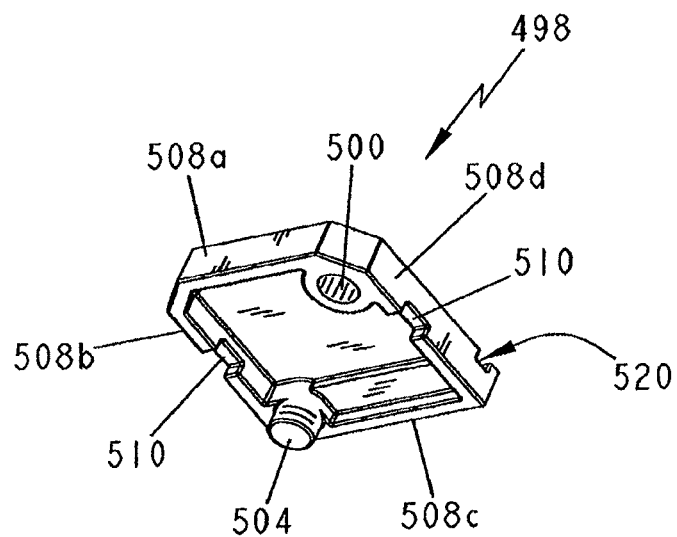
FIG. 20 is a perspective view of a base of the housing of FIG. 18.
Figure 21:
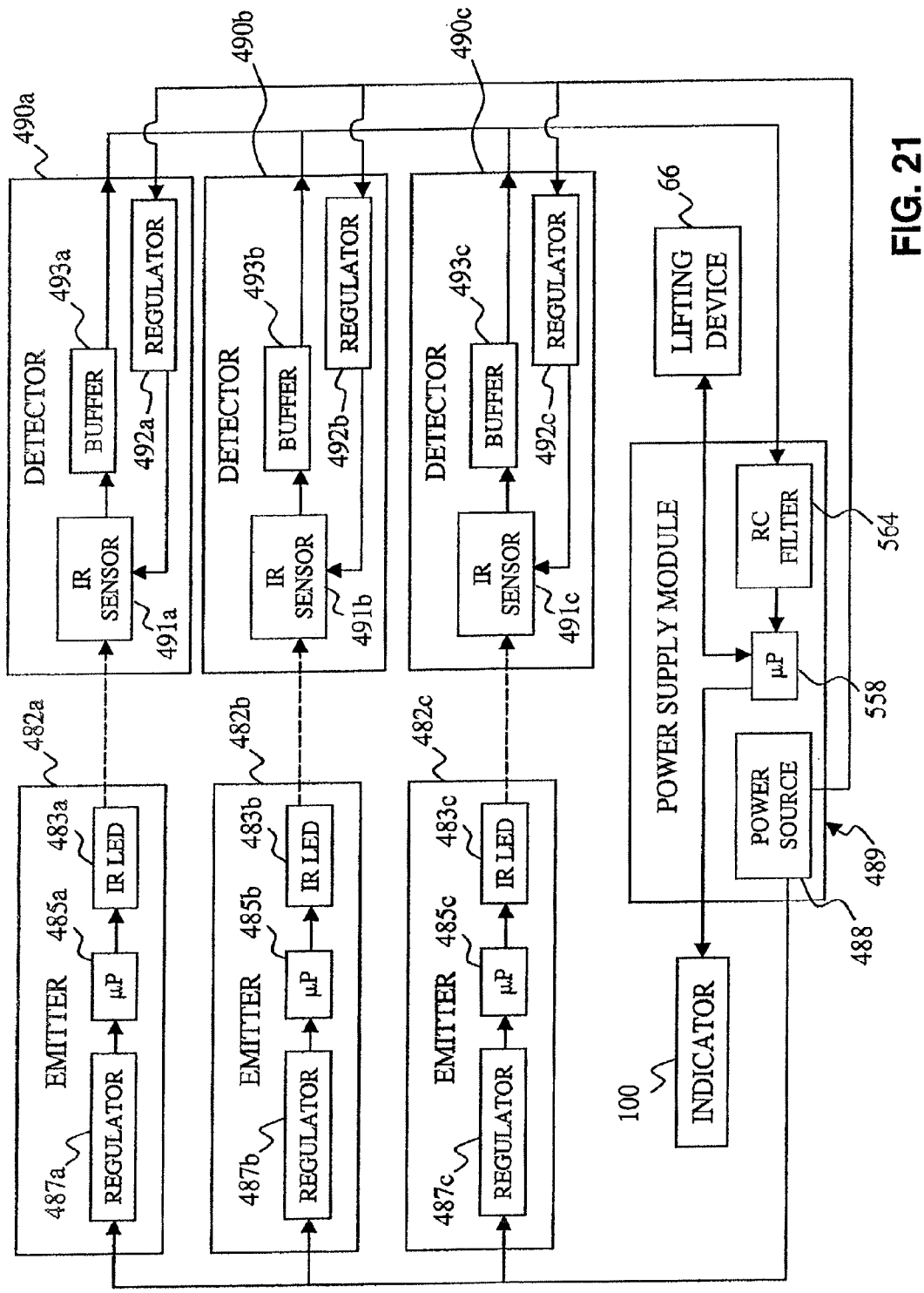
FIG. 21 is a block diagram representation of the obstacle detection device of FIG. 12.

FIGS. 12 and 13, illustrate portions of a hospital bed 410 including a further illustrative embodiment obstacle detection device 412 of the present invention. The obstacle detection device 412 includes a first or right side detection unit 470 associated with the right longitudinal side edge 14 of the hospital bed 410, a second or left side detection unit 472 associated with the left longitudinal side edge 16 of the bed 310, and a third or foot end detection unit 474 associated with the foot end 20 of the bed 310. The right side detection unit 470 is configured to detect an obstacle proximate the top of the right side member 21 of the base frame 24, while the left side detection unit 472 is configured to detect an obstacle along the top of the left side 23 of the base frame 24. Likewise, the foot end detection unit 474 is configured to detect an obstacle in front of the foot end cross member 29 of the base frame 24 at the foot end 20 of the bed 410. It should be appreciated that a fourth or head end detection unit (not shown) may be provided adjacent the head end 18 of the bed 410 for detecting an obstacle behind the head end cross member 31 of the base frame 24 of the bed 410.

As shown in FIGS. 13-15 and 21, each detection unit 470, 472, 474 of the obstacle detection device 412 includes an emitter 482a, 482b, 482c and an associated detector 490a, 490b, 490c. Each emitter 482 illustratively comprises a self-contained infrared (IR) light-emitting diode (LED) 483 coupled to an emitter microprocessor 485 which generates an infrared (R) signal that is configured to be received by the associated detector 490. The microprocessor 485 illustratively comprises a conventional eight-bit microprocessor and may comprise Part No. MC68HC908QT1CDW available from Motorola of Schaumburg, Ill. A voltage regulator 487 is used to interface the microprocessor 485 to an 8.2 volt input provided by the power source 488 of a power supply module 489. The output of the microprocessor 485 interfaces with the LED 483, which converts the electrical signal into an optical one.

The detector 490 includes an IR sensor 491 which is configured to receive the optical signal emitted from the emitter 482 and convert the optical signal to an electrical signal. Illustratively, the sensor 491 is an infrared photo diode configured to observe a specific signal frequency and may comprise infrared detector Part No. GP1UM267XK available from Sharp Microelectronics of Camas, Wash. The IR sensor 491 is interfaced to the 8.2 volt power source 488 via a conventional regulator 492. The output of the detector 490 is routed through a buffer 493 and to the power supply module 489 for processing in the manner described herein.

While the illustrative emitters 482 and detectors 490 utilize infrared light, it should be appreciated that other wireless signals may be substituted therefore. More particularly, other forms of electromagnetic radiation, such as ultrasonic, radar, and microwave, may be substituted for IR light.

With reference to FIGS. 12, 13, and 16-20, each emitter 482 and detector 490 is received within a housing 494. Each housing 494 includes a cover 495 coupled to a base 498. The base 498 includes a mounting aperture 500 configured to receive a fastener 502 for securing the base 498 to an aperture 503 formed in the base frame 24 of the bed 410. A locating peg 504 extends downwardly from a lower surface of the base 498 and is configured to be received within an aperture 506 formed in the base frame 24 of the bed 410. As such, the combination of the fastener 502 received within the aperture 503 and the locating peg 504 received within the aperture 506 provides for the proper orientation and coupling of the housing 494 relative to the base frame 24. The base 498 further includes four side walls 508 having a pair of notches or slots 510 formed in a pair of opposing ones of the side walls 508b and 508d.

The cover 496 includes four side walls 512 and a top wall 514. A pair of locking tabs 516 are resiliently supported by an opposing pair of the side walls 512b and 512d and are configured to lockingly engage with the notches 510 of the base 498. Cooperating slots 518 and 520 are formed within the cover 496 and base 498 and are configured to receive components, as supported on a circuit board 522, of the respective emitter 482 and detector 490. A pair of apertures 524 are formed within one of the side walls 512a of the cover 496 and are aligned with the LED 483 of the emitter 482 or the sensor 491 of the detector 490. The apertures 524 are positioned and sized for the efficient transmission of infrared light without incurring substantial interference from external light sources. Illustratively, the apertures 524 have a diameter of 3.18 millimeters (0.125 inches) and are positioned approximately 24.2 mm (0.953 inches) in front of the mounting slots 518 and 520 for the respective circuit board 522.

With reference to FIGS. 12, 13, 16, and 17, the respective housings 440 are protected from fluid ingress by caster or frame covers 526, 528, 530 that cover portions of the base frame 24 proximate the head and foot ends 18 and 20. Each head end frame cover 526 and 528 includes a housing 531 having side walls 532 connected to a top wall 534. One of the side walls 532 includes an opening 536 aligned with one of the apertures 524 in one of the housings 494 associated with the right and left side detection units 470 and 472. A transparent window 538, illustratively a clear thermoplastic material, is fixed within the opening 536 to prevent the passage of fluid therethrough, while permitting the passage of infrared light from the emitter 482 to the detector 490. The window 538 may be fixed in place using conventional methods, such as ultrasonic welding or adhesives. A clearance slot 540 may be formed in another one of the side walls 532 of the frame covers 526 and 528 to provide clearance for the brake/steer pedals 542 of the hospital bed 410, as needed.

The foot end frame cover 530 includes first and second housings 544 and 546 coupled together by a connecting member 548. Each housing 544 and 546 includes side walls 550 coupled to a top wall 552, and a pair of openings 554 and 556 formed within different ones of the side walls 550. The openings 554 are associated with one of the apertures 524 of the foot end housings 494 of the right and left side detection units 470 and 472. The openings 556 are associated with one of the apertures 524 of the housings 494 associated with the foot end detection unit 474. Windows 538 are illustratively fixed within the openings 554 and 556 as detailed above.

As illustrated in FIGS. 12 and 13, the right and left side detection units 470 and 472 may have their emitters 482 positioned at the head end 18 and foot end 20 of the hospital bed 410, respectively. As such, the transmission of infrared light from the emitters 482 of the right side detection unit 470 and the left side detection unit 472 will be in opposite directions (as shown by arrows 557 in FIG. 13) in order to reduce the possibility of cross talk between the two detection units 470 and 472. Likewise, the emitter 482 of the foot end detection unit 474 does not direct infrared light toward the detectors 490 of the right and left side detection units 470 and 472.

Figure 22:
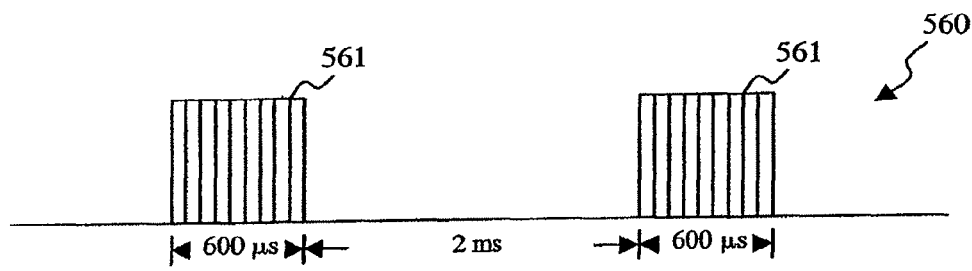
FIG. 22 is a timing diagram of an illustrative signal generated by the emitter of the obstacle detection device of FIG. 12.

To begin operation of the obstacle detection device 412, a controller or microprocessor 558 of the power supply module 489 initializes the various parameters and disables all interrupts. The power source 488 of the power supply module 489 supplies each emitter 482 with the required power of 8.2 volts. The microprocessor 485 of each emitter 482 is used to cause the LED 483 to generate an IR pulse signal 560 of the type illustrated in FIG. 22. Illustratively, the signal 560 includes a 600 microsecond pulsed portion 561 having a 57 kHz signal with a 50 percent duty cycle. A two millisecond delay follows the 57 kHz pulse with the output low. Such a pulse sequence repeats indefinitely. An internal bus clock (not shown) illustratively runs at 3.2 MHz. As such, this provides an instruction cycle time of 312.5 nanoseconds.

The detector 490 is configured to look for a 056.8 diz signal, which translates into 17.66 microseconds per pulse, or 8.803 microseconds per state. The number of instruction cycles per state is determined by the following formula:

Instruction cycles=total time/instruction cycle time

By inserting the above values for total time of 8.803 microseconds and instruction cycle time of 312.5 nanoseconds, the number of instruction cycles is determined to be 28.17. Using 28 cycles per state provides a total pulse time of 17.5 microseconds which equates to 57.14 kHz. A loop that generates the 57 kHz IR signal is run 34 times, thereby giving a total time of 595 microseconds.

The detector 490 is configured to look for the pulse signal 560 including a pulsed portion or an IR signal burst 561 at a specific frequency. When the signal 560 is detected with the appropriate frequency component, the output of the detector 490 becomes active, effectively demodulating the transmitted signal. The detector 490 includes a built-in frequency filter having a range of 53.6 kHz to 60 kHz (56.8+3.2 kHz).

In addition to a band-pass filter, the IR detector 490 adjusts its sensitivity level proportionately to the strength of the incident light signal. This helps further filter noise signals that may be present in the 56.8 kHz range.

The IR detector 490 filters the incident light to allow only the wave length associated with IR to come into contact with the internal photo diode or sensor 491. This helps filter out the effects of sunlight, incandescent lighting, and fluorescent lights.

Figure 23:
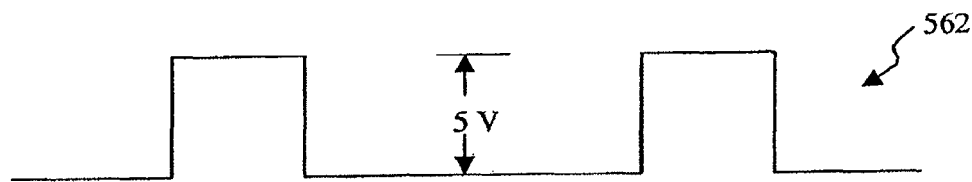
FIG. 23 is an illustrative waveform generated by the detector of the obstacle detection device of FIG. 12 in response to the illustrative signal of FIG. 22.

Upon detecting the appropriate wave length or frequency pulse signal 560, the detector 490 provides an essentially demodulated signal 562 such as that illustrated in FIG. 23. The signal illustratively has a high value of approximately 5 volts.

Figure 24:
FIG. 24 is an illustrative waveform as received by the microprocessor after the illustrative detector waveform of FIG. 23 passes through an RC filter.
Figure 25:
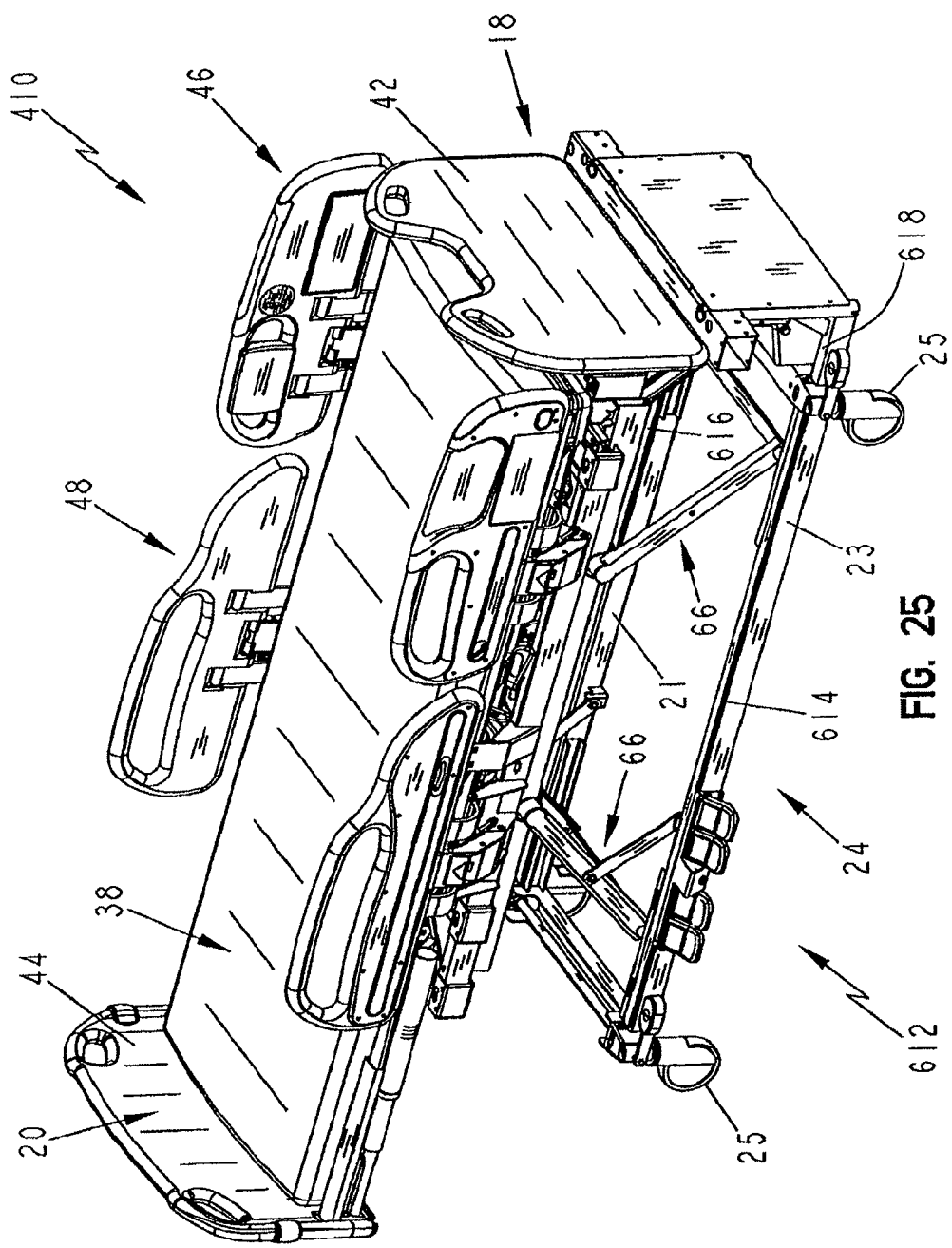
FIG. 25 is a perspective view of a hospital bed incorporating a further illustrative embodiment of the obstacle detection device of the present invention.
Figure 26:
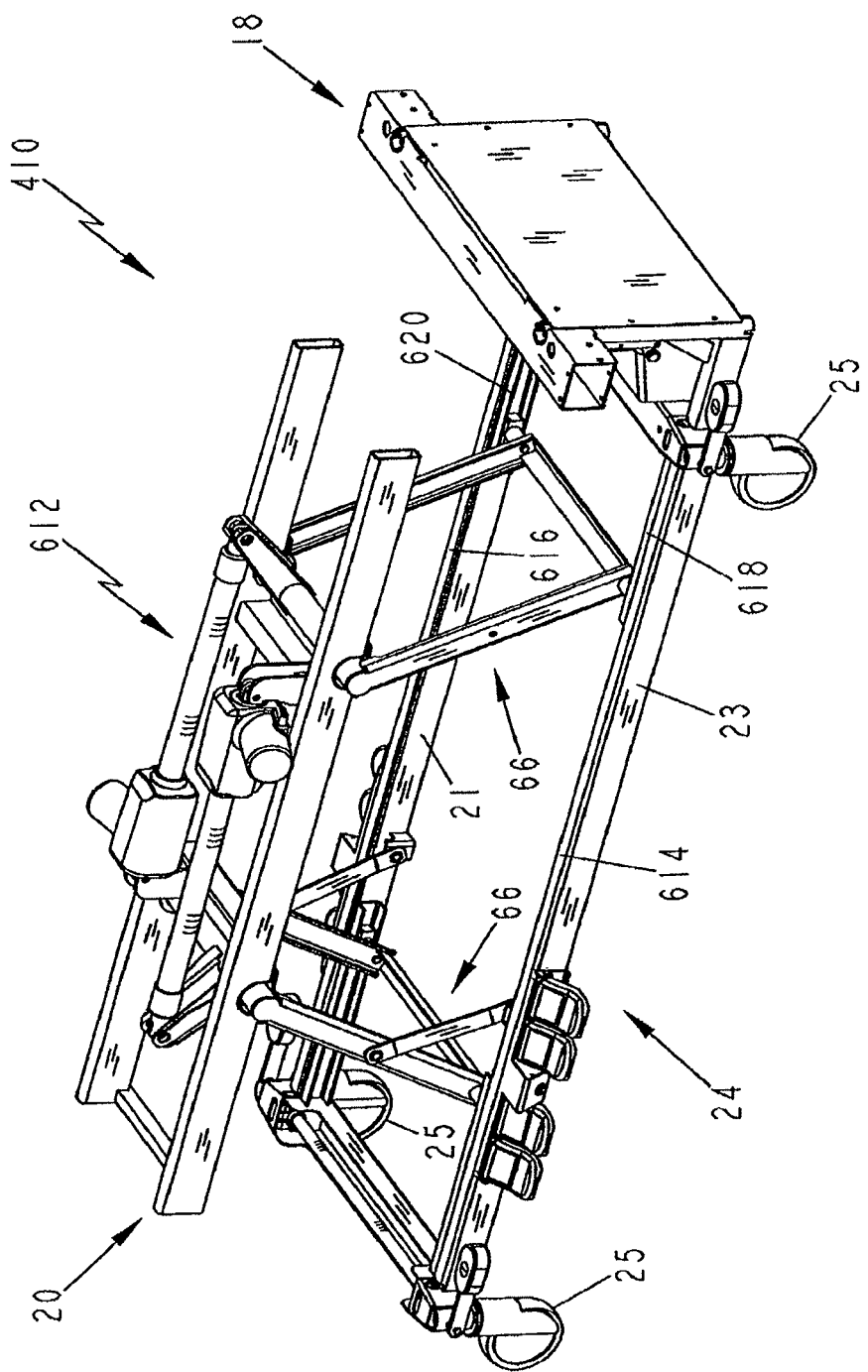
FIG. 26 is a perspective view of the hospital bed of FIG. 25 with certain components removed for clarity.
Figure 27:
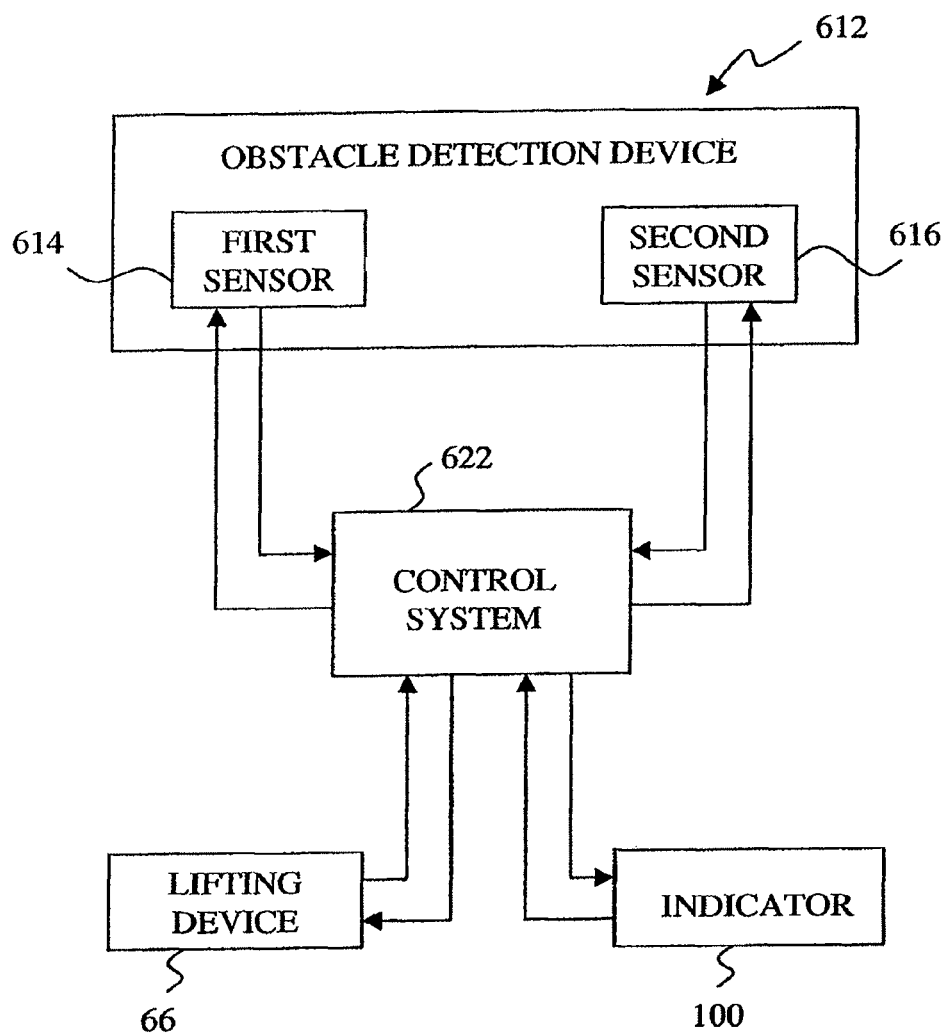
FIG. 27 is a block diagram representation of the obstacle detection device of FIG. 25.

The demodulated signal 562 from the detector 490 is then transmitted to a Resistor-Capacitor (RC) filter 564 comprising part of the power supply module 489. The RC filter 564 converts the signal 562 of FIG. 23 to a waveform 566 such as that illustrated in FIG. 24. The waveform of FIG. 24 has a nominal value of approximately 3.8 volts.+−.0.5 volts. Illustratively, the RC filter 564 is of conventional design and includes a 100 kohm resistor and a 0.1 μF capacitor. The output from the RC filter 564 passes through a conventional analog to digital (A/D) converter (not shown) on its way to the microprocessor 558.

If the RC filter output drops below 3.3 volts, then the microprocessor knows that an obstacle has blocked the IR light path between the emitter 482 and the detector 490, or that a fault condition exists, such as the emitter 482 or detector 490 not functioning properly. In either case, the microprocessor 558 functions by activating an indicator 100 and disabling the lifting device 66 from further lowering of the patient support as detailed herein.

It should be appreciated that each emitter 482 and detector 490 could be configured to send and receive signal waveforms having different bit or pulse patterns, including different pulse frequencies and pulse durations, in order to further limit the possibility of cross talk between different emitters and detectors. As may be appreciated, since the detectors 490 are configured to detect a frequency rather than an intensity, interference from external light sources is reduced. Furthermore, by looking for frequency, similar emitters 482 and detectors 490 may be used for obstacle detection for a wide range of distances between the respective emitters 482 and detectors 490.

Referring now to FIGS. 25-30, a further illustrative embodiment obstacle or interference detection device 612 is shown coupled to the base frame 28 of the patient support 410. The interference detection device 612 illustratively includes first and second sensors 614 and 616 which are coupled to upper surfaces 618 and 620 of the longitudinally extending first (right) and second (left) side members 25 and 27 of the base frame 24, respectively. While in the following description, first and second sensors 614 and 616 are illustrated as being associated with the side members 25 and 27 of the patient support 410, it should be appreciated that additional sensors could be positioned adjacent the head end 18 and the foot end 20 of the patient support 410.

Each sensor 614 and 616 is configured to provide an interference detection signal to a control system 622 in the event that it detects an obstacle or determines that a fault condition exists. More particularly, each sensor 614 and 616 is configured to provide the interference detection signal to control system 622 upon detecting that an object, such as an individual's foot, is supported on one of the upper surfaces 618 and 620 of the base frame 24. As described in greater detail below, the sensors 614 and 616 are configured to generate an interference detection signal only when a predetermined sufficient force is applied thereto or when a fault condition occurs. As such, the sensors 614 and 616 avoid generating false interference detection signals which could impact the normal operation of the patient support 410.

Figure 28:
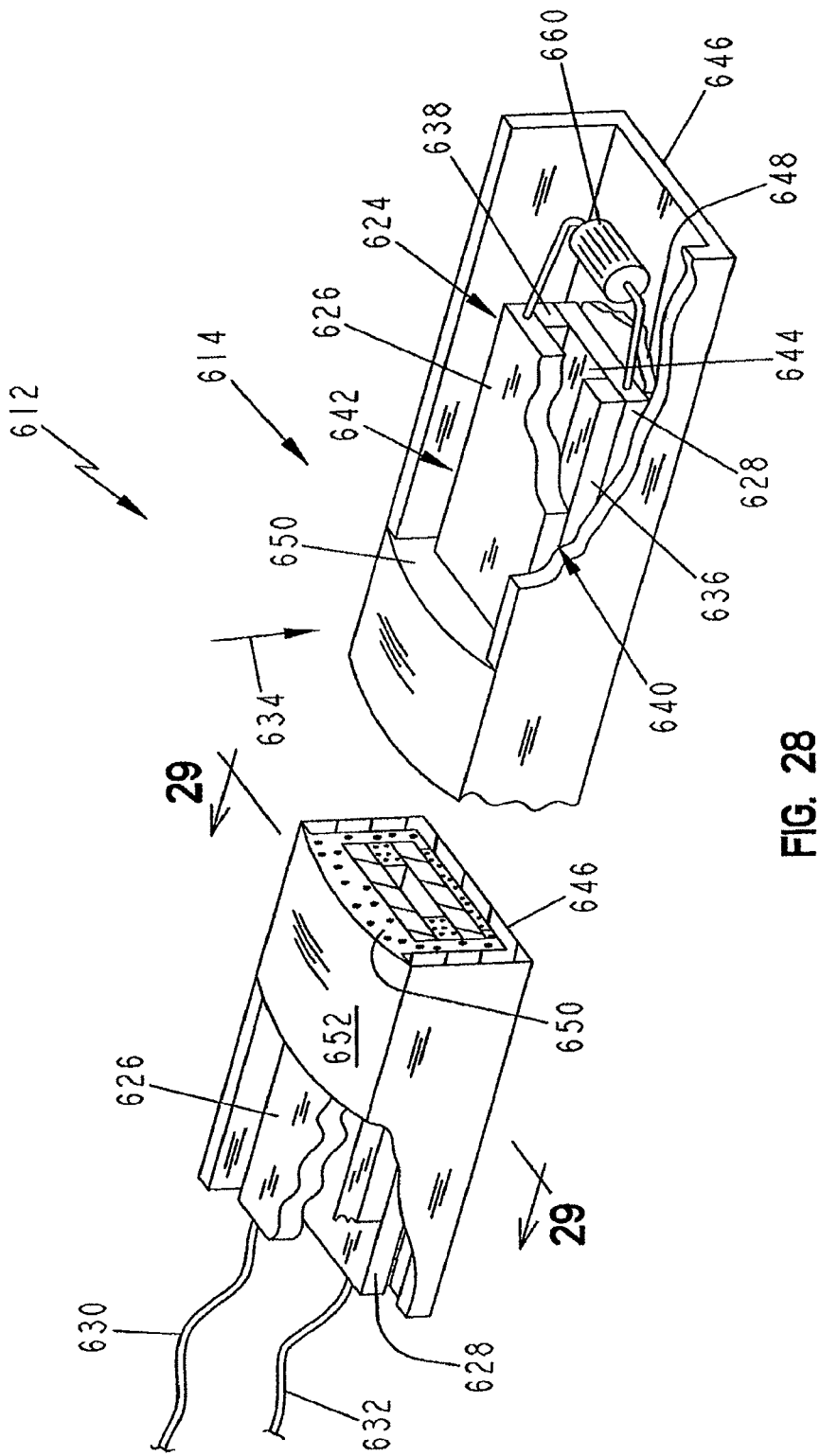
FIG. 28 is a detailed perspective view, with a partial cutaway, of a sensor of the obstacle detection device of FIG. 25.
Figure 29:
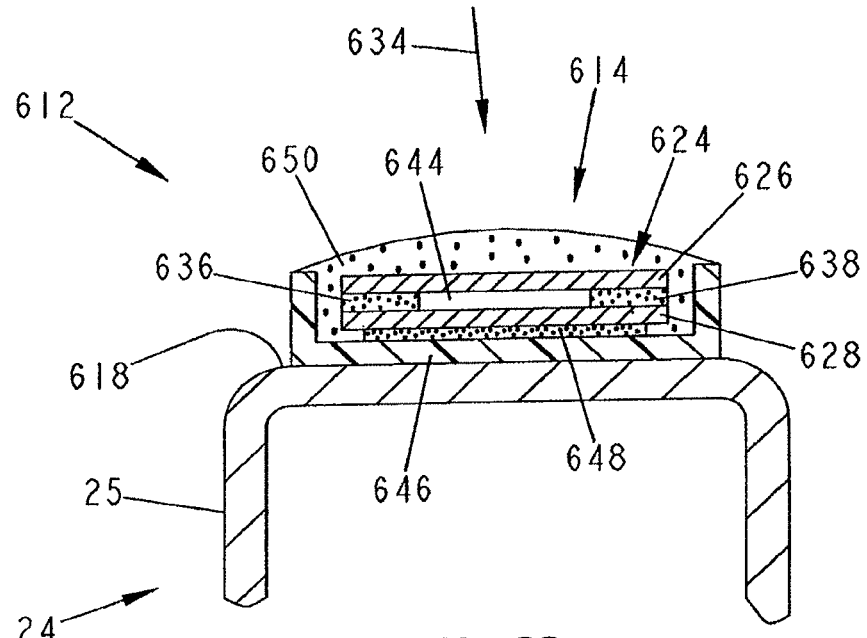
FIG. 29 is a cross-sectional view taken along lines 29-29 of FIG. 28.

Referring further to FIGS. 28 and 29, each sensor 614 and 616 illustratively includes a force sensing tape switch 624 including upper and lower contacts 626 and 628 which extend in substantially parallel relation in a longitudinal direction above the side members 25 and 27 of the base frame 24. Each contact 626 and 628 is electrically conductive and is in electrical communication with control system 622 through conventional wires 630 and 632, respectively. Further, the upper contact 626 is resilient so that a downwardly acting vertical force 634 will cause it to deflect into electrical contact with the lower contact 628, and upon removal of the force 634 the upper contact 626 will return to its original position in spaced relation to the lower contact 628. Illustratively, each contact 626 and 628 is formed from a thin sheet or layer of stainless steel. A pair of isolation spacers 636 and 638 are positioned intermediate the upper and lower contacts 626 and 628 along opposing longitudinally extending side edges 640 and 642 thereof. As such, the isolation spacers 636 and 638 define a central void 644 through which the upper contact 626 may be deflected into electrical contact with the lower contact 628. The isolation spacers 636 and 638 may be formed of any electrically insulative material, and are illustratively formed from either a Mylar® film or conventional adhesive.

The lower contact 628 is secured to a base 646, illustratively formed from an electrically insulative material to prevent electrical communication between the lower contact 628 and the base frame 24. An adhesive 648 may be utilized to secure the lower contact 628 to the base 646. In one illustrative embodiment, the base 646 is made from a thermoplastic material and formed as an unshaped channel. The base 646 is secured to a respective upper surface 618, 620 of the base frame 24, illustratively through the use of an adhesive, although other conventional fastening means, such as screw or bolts, may likewise be used. A potting compound 650, illustratively an epoxy, is received within the base 646 and encapsulates the switch 624 formed by the upper and lower contacts 626 and 628 and the isolation spacers 636 and 638.

As illustrated in FIGS. 28 and 29, the potting compound 650 does not fill the void 644 between the upper and lower contacts 626 and 628. Further, the potting compound 650 defines an upper surface 652 of the sensor 614. The material and dimensions of the potting compound 650 and the upper contact 628 are selected to provide a sufficient resiliency such that when a predetermined sufficient force is applied to the upper surface 652, the potting compound 650 causes the upper contact 626 to move downwardly into electrical communication with the lower contact 628. In an illustrative embodiment, the predetermined sufficient force is set to be approximately 3.4 lbs.

Each sensor 614 and 616 is configured to detect not only a force exerted by an obstacle, but also a switch fault condition. More particularly, each sensor 614 and 616 is configured to provide a logic high value to control system 44 when an obstacle is not detected, and the switch 624 is open, and a logic low value when an obstacle is detected, and the switch 624 is closed. Based on the signal received from the obstacle detection device 612, control system 622 will prevent the lowering of the intermediate or elevating frame 26 relative to the base frame 24. More particularly, the logic low value represents the interference detection signal to control system 622. As detailed below, this logic low value may occur when the switch 624 is closed or when the switch 624 is in a fault condition.

Figure 30:
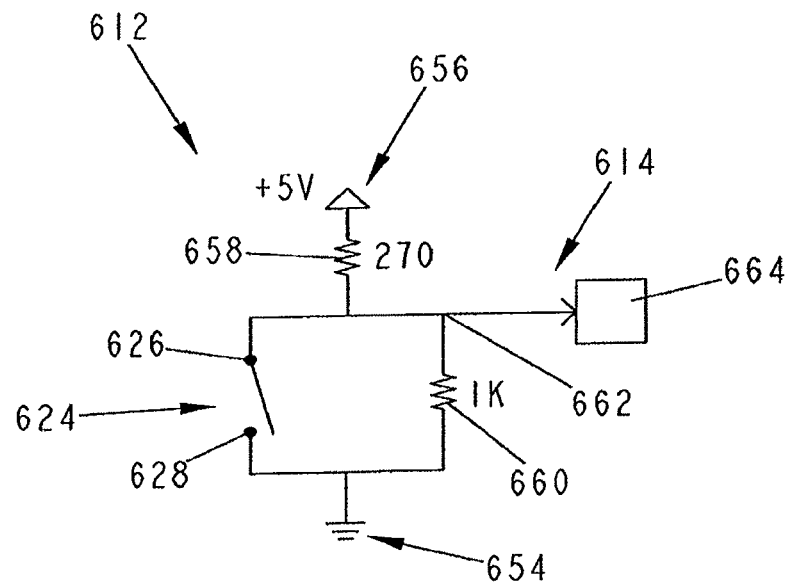
FIG. 30 is a diagrammatic representation of the obstacle detection device of FIG. 25.

Referring to FIG. 30, a schematic representation of the first sensor 614 of the obstacle detection device 612 is shown. It should be appreciated that the second sensor 616 is substantially identical. The upper and lower contacts 626 and 628 are shown as embodied within the switch 624. As stated previously, the upper and lower contacts 626 and 628 are made of an electrically conductive material and are spaced apart at their sides edges 640 and 642 by isolation spacers 636 and 638. However, the upper and lower contacts 626 and 628 are capable of contacting each other within the central void 644 positioned between the contacts 626 and 628. As detailed above, the upper contact 626 is configured to contact the lower contact 628 when an obstacle exerts a sufficient force against the upper surface 652 of the potting compound 650. As such, the switch 624 is open when the upper and lower contacts 626 and 628 remain spaced apart, and the switch 624 is closed when the upper contact 626 is brought into contact with the lower contact 628 by the application of a sufficient downward force against the upper surface 652.

As shown in FIG. 30, the lower contact 628 is electrically connected to a ground 654. The upper contact 626 is connected to a voltage supply 656 through a first resistor 658, illustratively having a value of 270 ohms. The voltage supply 656 may form part of the control system 622. Further, the upper and lower contacts 626 and 628 are connected together by a second resistor 660, illustratively having a value of 1 kohm. A voltage output signal 662 is taken at the upper contact 626 and then sent to an Analog to Digital (A/D) converter 664 to generate a logic signal for control system 622. The A/D converter 664 may be incorporated within the control system 622.

When the force exerted by an obstacle does not bring the upper contact 626 into contact with the lower contact 628, the switch 624 is open and the circuit shown in FIG. 30 is a voltage divider. In an illustrative embodiment, the voltage supply 656 is a five volt supply and the values of first and second resistors 658 and 660 are selected such that a voltage value corresponding to a high logic value is measured at the upper contact 626. In one embodiment, the measured voltage is 3.9V. When an obstacle brings the upper contact 626 in contact with the lower contact 628, the switch 624 is closed and the entire voltage of the voltage supply 656 is dropped over the first resistor 658 such that the voltage value measured at the upper contact 626 corresponds to a logic low value. Likewise, should a break or similar fault occur within the switch 624, the voltage of the voltage supply 656 is dropped over the first resistor 658 such that the voltage value measured at the upper contact 626 will correspond to a logic low value. In any of these situations, whether the switch 624 is open, the switch 624 is closed, or the switch 624 is in a fault condition, the A/D converter 664 converts the analog voltage signal measured at the upper contact 626 and converts it into either a logic high value or a logic low value.

In response to the interference detection signal as represented by a logic low value, control system 622 will prevent the lowering of the elevating frame 26 relative to the base frame 24. Moreover, the logic low value indicates that either an obstacle is supported on the base frame 24 or that the switch 624 is not operating properly and is in a fault condition. As such, in order to avoid potential damaging impact with the detected obstacle, control system 622 prevents lifting device 66 from operating to lower the elevating frame 26. In an illustrative embodiment, control system 622 permits continued operation of the lifting device 66 to raise the elevating frame 26. Further, upon receiving the interference detection signal, control system 622 may instruct the lifting device 66 to raise the elevating frame 26 for a predetermined time period, illustratively 2 seconds, while preventing operation of the lifting device 66 to lower the elevating frame 26. Raising the elevating frame 26 for a time period after an obstacle has been detected, provides for the immediate and automatic movement of the frame 26 in a direction away from the detected obstacle.

While the sensors 614 and 616 of the interference detection device 612 are illustratively positioned on the base frame 24, it should be appreciated that the sensors 614 and 616 could likewise be positioned on a lower surface of the elevating frame 26. Further, the interference detection device 612 may be utilized to detect obstacles between any two portions of a patient support apparatus which move relative to each other. For example, the interference detection device 612 may be used between the foot end and head end siderails 46 and 47, between the head end siderails 47 and the headboard 42, and between the foot end siderails 46 and the footboard 44.

In a further alternative embodiment of the obstacle detection device 12 of the present invention, the detectors 90, 92, 94 may comprise cameras utilizing vision technology to detect obstructions. More particularly, the camera captures images as the elevating frame 26 moves along its path of travel. The images captured by the camera are compared by the control unit 98 to predefined images of the elevating frame 26 moving along the path of travel with no obstructions present. If each captured image fails to substantially match a corresponding predefined image, then the control unit 98 generates the stop signal 108 to prevent movement of the elevating frame 26 in the manner detailed above.

In yet another illustrative embodiment of the obstacle detection device 12 of the present invention, the detectors 90, 92, 94 may comprise conductors, such as fiber optic cables, each having a property that changes between a first state and a second state upon movement of bed frame components. Additional details of such a conductor are disclosed in U.S. patent application Ser. No. 09/791,936, filed Feb. 23, 2001, now U.S. Pat. No. 6,662,391, which is assigned to the assignee of the present invention and which is expressly incorporated by reference herein.

While the foregoing illustrative description details application of the obstacle detection device 12 of the present invention for detecting an obstacle between an elevating frame 26 and a base frame 24, this in no way is intended to limit the scope of the invention. Moreover, the obstacle detection device 12 may be utilized to detect obstacles between any two portions of a patient support apparatus which move relative to each other. For example, the obstacle detection device 12 may be used between the first and second siderails 46 and 47, between the first siderail 46 and the footboard 44, and between the second siderail 47 and the headboard 42.

Although the invention has been described in detail with reference to certain illustrated embodiments, variations and modifications exist within the scope and spirit of the invention as described and as defined in the following claims.

The invention claimed is:

1. A patient support apparatus comprising
a base frame including an elongated base frame member having an upper surface,
an elevating frame disposed in spaced relation to said base frame,
a lifting device configured to move said elevating frame relative to said base frame,
an emitter arranged to emit a light beam that is located above the upper surface of the base frame member and that is generally parallel with the upper surface of the base frame member,
a receiver arranged to receive the light beam emitted from the emitter, wherein the lifting device is disabled if an obstacle blocks the light beam emitted by the emitter from being received by the receiver, and
a second base frame member having a second upper surface, a second emitter arranged to emit a second light beam that is located above the second upper surface of the second base frame member and that is generally parallel with the second upper surface of the second base frame member, and a second receiver arranged to receive the light beam emitted from the second emitter, wherein the lifting device is disabled if an obstacle blocks the second light beam emitted by the second emitter from being received by the second receiver, wherein the second base frame member is parallel with and spaced from the first base frame member, wherein the first base frame member and the second base frame member each have first and second ends, the first emitter being coupled to the first end of the first base frame member and the second emitter being coupled to the second end of the second base frame member such that light is emitted in opposite directions from the first and second emitters.

2. The patient support apparatus of claim 1, wherein the light beam is emitted as a pulsed signal.

3. The patient support apparatus of claim 1, wherein the light beam comprises an infrared light beam.

4. The patient support apparatus of claim 1, wherein the emitter is supported by the base frame member.

5. The patient support apparatus of claim 1, wherein the receiver is supported by the base frame member.

6. The patient support apparatus of claim 1, wherein the emitter comprises an infrared light emitting diode.

7. The patient support apparatus of claim 1, wherein the receiver comprises an infrared sensor.

8. The patient support apparatus of claim 1, wherein the second base frame member is parallel with and spaced from the first base frame member.

9. A patient support apparatus comprising
a base frame including an elongated base frame member having an upper surface,
an elevating frame disposed in spaced relation to said base frame,
a lifting device configured to move said elevating frame relative to said base frame,
an emitter arranged to emit a light beam that is located above the upper surface of the base frame member and that is generally parallel with the upper surface of the base frame member,
a receiver arranged to receive the light beam emitted from the emitter, wherein the lifting device is disabled if an obstacle blocks the light beam emitted by the emitter from being received by the receiver, and
a second base frame member having a second upper surface, a second emitter arranged to emit a second light beam that is located above the second upper surface of the second base frame member and that is generally parallel with the second upper surface of the second base frame member, and a second receiver arranged to receive the light beam emitted from the second emitter, wherein the lifting device is disabled if an obstacle blocks the second light beam emitted by the second emitter from being received by the second receiver, wherein the base frame includes an end base frame member that is perpendicular to the base frame member and further comprising a third emitter that emits a third light beam adjacent the end base frame member and a third receiver arranged to receive the third light beam, wherein the lifting device is disabled if an obstacle blocks the third light beam emitted by the third emitter from being received by the third receiver.

10. The patient support apparatus of claim 9, wherein the base frame member has a first end and a second end, the emitter being located adjacent the first end and the receiver being located adjacent the second end such that the light beam is located over a majority of a length of the base frame member.

11. The patient support apparatus of claim 9, wherein the end base frame member is situated near a foot end of the base frame.

12. The patient support apparatus of claim 9, further comprising a first cover that shrouds the emitter and a second cover that shrouds the receiver.

13. The patient support apparatus of claim 12, wherein the first and second shrouds each include an opening to allow passage of the light beam therethrough.

14. The patient support apparatus of claim 9, wherein the upper surface of the base frame member comprises a generally planar surface.

15. The patient support apparatus of claim 9, wherein the base frame includes a first caster and a second caster, the emitter is located near the first caster, and the receiver is located near the second caster.

16. The patient support apparatus of claim 15, wherein the first caster is located adjacent a head end of the base frame and the second caster is located adjacent a foot end of the base frame.

17. The patient support apparatus of claim 9, wherein the first caster is located adjacent a foot end of the base frame and the second caster is located adjacent a head end of the base frame.

18. The patient support apparatus of claim 9, wherein the emitter is coupled to a base that couples to the base frame member via a fastener and a locating peg.

19. The patient support apparatus of claim 9, wherein the receiver is coupled to a base that couples to the base frame member via a fastener and a locating peg.

* * * * *